US011339374B2

(12) United States Patent
Dimmock et al.

(10) Patent No.: US 11,339,374 B2
(45) Date of Patent: May 24, 2022

(54) ASSAY AND MEDICAMENT

(71) Applicant: The University of Warwick, Coventry (GB)

(72) Inventors: Nigel J. Dimmock, Coventry (GB); Andrew J. Easton, Coventry (GB)

(73) Assignee: The University of Warwick, Coventry (GB)

( * ) Notice: Subject to any disclaimer, the term of this patent is extended or adjusted under 35 U.S.C. 154(b) by 0 days.

(21) Appl. No.: 16/230,114

(22) Filed: Dec. 21, 2018

(65) Prior Publication Data

US 2020/0231939 A1 Jul. 23, 2020

Related U.S. Application Data

(63) Continuation of application No. 15/111,615, filed as application No. PCT/GB2015/050094 on Jan. 16, 2015, now abandoned.

(30) Foreign Application Priority Data

Jan. 16, 2014 (GB) ..................... 1400752

(51) Int. Cl.
*C12N 7/00* (2006.01)
*C12Q 1/70* (2006.01)
*C12N 7/04* (2006.01)

(52) U.S. Cl.
CPC ............... *C12N 7/00* (2013.01); *C12N 7/045* (2013.01); *C12Q 1/701* (2013.01); *C12N 2760/16132* (2013.01); *C12N 2760/16162* (2013.01)

(58) Field of Classification Search
None
See application file for complete search history.

(56) References Cited

U.S. PATENT DOCUMENTS

| 2007/0202492 | A1* | 8/2007 | Easton | C12Q 1/6897 435/5 |
| 2009/0191158 | A1* | 7/2009 | Dimmock | C07K 14/005 424/93.6 |

FOREIGN PATENT DOCUMENTS

| WO | 2006051069 A2 | 5/2006 | |
| WO | WO-2006051069 A2 * | 5/2006 | ............... C12N 7/00 |

OTHER PUBLICATIONS

Duhaut et al., Defective RNAs Inhibit the Assembly of Influenza Virus Genome Segments in a Segment-Specific Manner (Virology, 1996, 216:326-337) (Year: 1996).*
Saira et al. Sequence Analysis of In Vivo Defective Interfering-Like RNA of Influenza A H1N1 Pandemic Virus. (JVI, 2013, 14:8064-8074) (Year: 2013).*
Odagiri et al., Segment-Specific Noncoding Sequences of the Influenza Virus Genome RNA Are Involved in the Specific Competition between Defective Interfering RNA and Its Progenitor RNA Segment at the Virion Assembly Step (J Virology, 1997, 71:2138-2145) (Year: 1997).*

(Continued)

*Primary Examiner* — Arthur S Leonard
(74) *Attorney, Agent, or Firm* — Patrick M. Torre; Stites & Harbison, PLLC

(57) ABSTRACT

The invention relates to defective interfering viruses and defective interfering virus RNAs that are effective as antiviral agents. The invention also relates to methods for identifying defective interfering virus RNAs that can be used as effective antiviral agents.

8 Claims, 12 Drawing Sheets

Specification includes a Sequence Listing.

(56) References Cited

OTHER PUBLICATIONS

Scott, Paul D., et al., Defective interfering influenza virus confers only short-lived protection against influenza virus disease: Evidence for a role for adaptive immunity in DI virus-mediated protection in vivo; 2011, Vaccine, vol. 29, No. 38, pp. 6584-6591.

Hutchinson, Edward C., et al., Genome packaging in influenza A virus; Journal of General Virology (2010), 91, 313-328.

Marsh, Glenn A., et al., Highly Conserved Regions of Influenza A Virus Polymerase Gene Segments Are Critical for Efficient Viral RNA Packaging; Journal of Virology, vol. 82, Mar. 2008, p. 2295-2304.

Janda, J. Michael, et al., Defective Influenza Viral Ribonucleoproteins Cause Interference; Journal of Virology (1979), 697-702.

Meng, Bo, et al., Unexpected complexity in the interference activity of a cloned influenza defective interfering RNA; Virology Journal (2017) 14:138.

Smith, Claire M., et al, A Defective Interfering Influenza RNA Inhibits Infectious Influenza Virus Replication in Human Respiratory Tract Cells: A Potential New Human Antiviral; 2016 Viruses vol. 8, No. 8.

Dimmock, Nigel J., et al., Cloned Defective Interfering Influenza RNA and a Possible Pan-Specific Treatment of Respiratory Virus Diseases; Viruses 2015, 7, 3768-3788.

* cited by examiner

FIG. 3A Control

FIG. 3B 1/244 DI DNA 0.1 µg 0.5 µg 1.0 µg

FIG. 3F Segment 6 DNA

FIG. 3C 2/265 DI DNA 0.1 µg 1.0 µg

FIG. 3D 3/262 DI DNA

FIG. 3E Segment 4 DNA

FIG. 7A
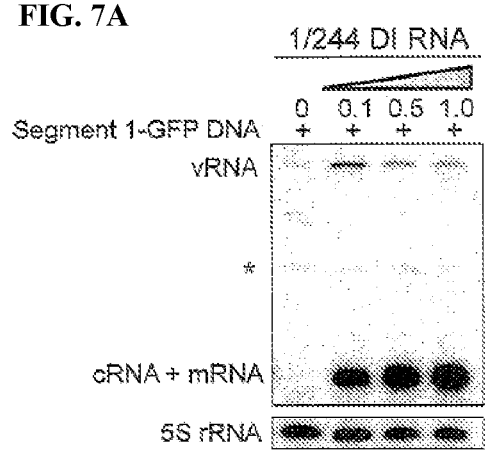
FIG. 7B
FIG. 7C
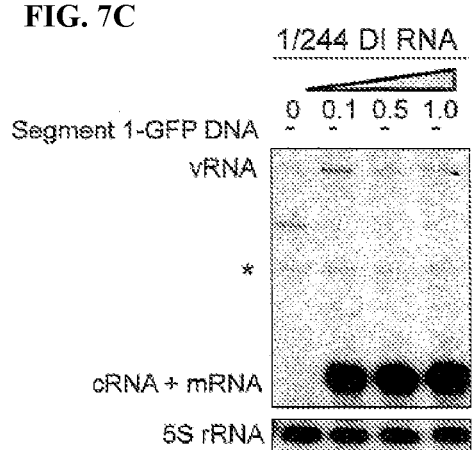
FIG. 7D
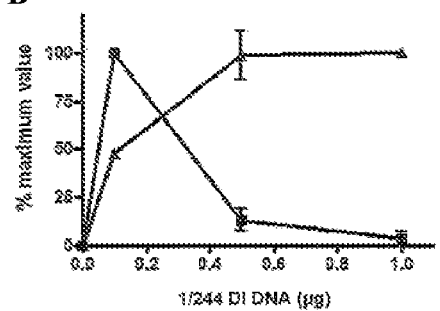
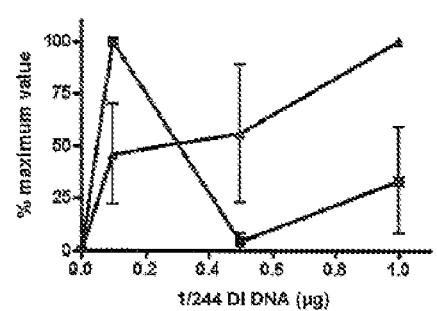

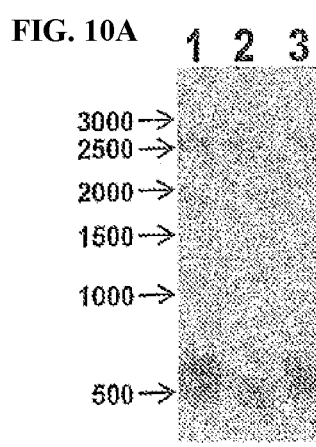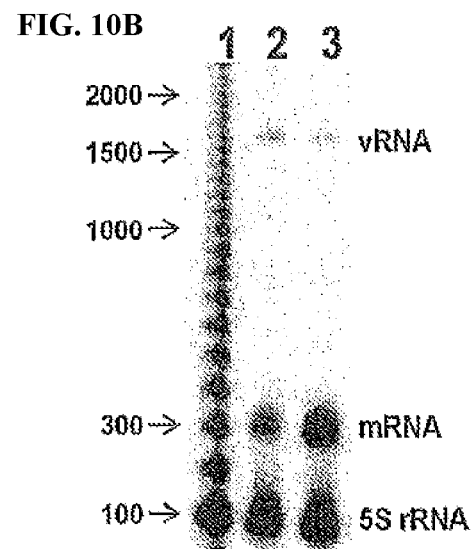
FIG. 10A
FIG. 10B

FIG. 11B 244 DI

FIG. 11C 244 AUG KO DI

ASSAY AND MEDICAMENT

CROSS REFERENCE TO RELATED APPLICATIONS

This application is a continuation of U.S. application Ser. No. 15/111,615, filed on Jul. 14, 2016, which is the national phase of International Patent Application No. PCT/GB2015/050094, filed Jan. 16, 2015, which claims priority to Great Britain Patent Application No. 1400752.0, filed Jan. 16, 2014, the entire disclosure of each of which is incorporated by reference herein for all purposes.

REFERENCE TO SEQUENCE LISTING SUBMITTED ELECTRONICALLY

A sequence listing electronically submitted with U.S. patent application Ser. No. 15/111,615 as an ASCII text file named 1944-SeqList.txt, created on Jul. 14, 2016 and having a size of 32000 bytes is incorporated herein by reference in its entirety.

FIELD OF THE INVENTION

The present invention relates to methods for identifying an antiviral agent, and in particular, to methods for assaying a defective interfering virus RNA to identify an antiviral agent. The invention also relates to new defective interfering viruses that are effective as antiviral agents.

BACKGROUND OF THE INVENTION

The influenza A genome comprises 8 segments of single stranded negative-sense RNA (vRNA) in the form of ribonucleoprotein (RNP) complexes. Inclusion of one copy of each of the 8 segments is required to make an infectious virus particle.

During the course of viral replication, progeny genomes can be generated that contain extensive deletions. At least some of such truncated genomes contain the signals necessary for packaging the nucleic acid into virus particles. However, the truncated genomes themselves are unable to generate infectious virus particles and are thus functionally defective. Some defective genomes are capable of interfering with the growth of the parental virus from which they were derived. The ability of such defective interfering (DI) genomes to interfere with virus replication had led to the suggestion that they can be used as the basis for a new approach to antiviral therapy.

Influenza virus infections can generate small DI RNA segments which can interfere with virus replication. Most influenza DI RNAs have a major (approximately 80%) internal deletion, and retain the cis-acting signals required for replication and packaging into virus particles. DI RNA is incorporated into a DI virus particle but the resulting DI virus particle cannot replicate autonomously since the deleted RNA is unable to synthesize the protein normally encoded by the full length segment. Hence, replication of a DI virus requires complementation by infectious virus.

Influenza virus genome replication commences with synthesis of positive-sense (cRNA) copies of the vRNA segments of the infecting virus, and these in turn are used as templates for synthesis of new vRNAs. vRNAs are also used as the template for mRNA transcription. Unlike cRNA synthesis, mRNA synthesis is initiated using a primer cleaved from the capped 5' end of host mRNA and its synthesis terminates before the end of the template vRNA, prior to polyadenylation. Thus the mRNA differs from the positive sense replication intermediate cRNA in having the primer-derived 5'-extension, and in being truncated and polyadenylated at the 3' end. The non-coding termini of each segment are crucial for RNA synthesis, and contain conserved, approximately 12 nucleotide (nt) sequences at the 5' ends which are almost exactly complemented at the 3' ends.

The synthesis of influenza virus RNA is carried out by a virus-encoded RNA dependent RNA polymerase present within each RNP complex that consists of the vRNA or cRNA strongly associated with the virus nucleoprotein (NP). The viral RNA polymerase comprises a heterotrimer of PB1, PB2 and PA proteins, which are encoded by vRNA segments 2, 1 and 3, respectively. Little progress has been made towards understanding the mechanism of interference by DI viruses generated by deletion. For DI RNAs generated by a central deletion, interference with RNA synthesis could involve specific competition between the DI RNA from which it is derived and genomic RNA for a limiting viral or host factor(s), and/or the much shorter DI RNA may have a more rapid rate of synthesis than its cognate genomic RNA giving it a competitive advantage, although there is little experimental evidence to support this.

Most studies of DI influenza virus-mediated interference to date have been carried out with naturally occurring preparations, and are compromised by the presence of mixtures of several different defective RNA sequences. This problem has been solved recently using reverse genetics to generate virus stocks containing a molecularly defined DI RNA (Dimmock et al. 2008). One such DI RNA is 1/317, derived from segment 1 of an avian H7N7 influenza A virus. This was present in a non-cloned virus that interfered with RNA packaging but had no discernible effect on viral RNA synthesis (Duhaut and McCauley 1996). Although the cloned 1/317 DI RNA, delivered intranasally as an influenza virus particle, has protective activity in mice, it was 100-fold less active than 1/244 DI RNA, derived from segment 1 of a human H1N1 virus, in the same delivery system (Dimmock et al. 2008). Inoculation of mice with 1/244 DI virus conferred complete protection from a lethal challenge with several different subtypes of influenza A virus (homologous protection) (Dimmock et al. 2008). However, the molecular basis of protection by 1/244 DI virus is not known. In addition to protection from influenza A viruses, 1/244 DI virus also protects from the heterologous influenza B virus and a murine paramyxovirus in a dose-dependent manner (Easton et al. 2011; Scott et al. 2011). Heterologous (but not homologous) protection is dependent on interferon type I.

SUMMARY OF THE INVENTION

The present invention has identified that the effectiveness of a DI influenza A virus to interfere with influenza A virus replication can be attributed to the ability of the DI virus RNA to interfere with production of RNA not only from the segment from which the DI virus RNA is derived, but also to interfere with production of RNA from all of segments 1, 2 and 3. As such, the present invention provides new methods for identifying defective interfering viruses that can be used as effective antiviral agents. Also, we provide novel defective interfering viruses.

The present invention has also identified that protein production from the DI virus RNA is not required for interfering activity. Accordingly, the present invention is also directed to a DI virus RNA in which the deleted segment RNA is further mutated to prevent expression of protein, for example, by deletion or mutation of one or more initiation codons AUG.

In accordance with one aspect the invention provides A method to identify an antiviral agent comprises monitoring for the production of RNA from segments 1, 2 and 3 of influenza A virus in the presence of a test defective interfering influenza virus RNA, wherein a defective interfering virus RNA that interferes with production of RNA from each of segment 1, 2 and 3 is identified as an antiviral agent.

In accordance with another aspect, the invention provides a cloned or recombinant defective interfering influenza A virus comprising RNA derived from segment 1, 2 or 3, wherein said RNA comprises:
  (a) an RNA of between 300 to 600 nucleotides in length;
  (b) at least 100 nucleotides from the 5' and 3' ends of segment 1, 2 or 3;
  (c) a central deletion of nucleotides of said segment;
    wherein said defective interfering influenza virus is capable of interfering with RNA production from segments 1, 2 and 3 of influenza A.

An antiviral agent identified in accordance with the present invention, or a defective interfering virus of the invention is also provided for use in a method of treatment or prophylaxis of influenza A infection. In another aspect, the present invention provides a defective interfering virus RNA, wherein the RNA is mutated to prevent expression of any encoded protein, for example, wherein one or more AUG initiation codons are mutated. Such a DI virus may be used in a method of treatment or prophylaxis of influenza A infection.

BRIEF DESCRIPTION OF THE FIGURES

FIG. 2 shows a northern blot analysis of influenza viral RNAs produced in the absence of and in the presence of influenza DI RNA. 293T cells were transfected with increasing amounts of the 1/244 DI PolI plasmid (0, 0.1, 0.5 and 1.0 µg) and a constant amount of the plasmids needed for the expression of infectious A/WSN virus (see text). After transfection, cells were co-cultivated with MDCK cells. RNA was extracted from co-cultured cells and from influenza virus particles purified from culture fluids.

FIG. 3 shows fluorescence assay analysis of expression of influenza segment 1 in the presence of influenza DI RNAs or other full-length influenza RNAs. 293T cells were transfected with the segment 1-GFP plasmid, plasmids expressing PB1, PB2, PA and NP proteins, and empty control vector (FIG. 3A) or increasing amounts of an additional PolI plasmid expressing 1/244 DI RNA (FIG. 3B), 2/265 DI RNA (FIG. 3C), 3/262-DI RNA (FIG. 3D), full-length segment 4 vRNA (FIG. 3E), or full-length segment 6 vRNA (FIG. 3F). At two days post transfection, cells were examined for fluorescence. Pairs of cell monolayer images taken by phase-contrast (left) and epifluorescence microscopy (right). The amount of each plasmid expressing the various RNAs used as putative inhibitors is shown on the left.

FIG. 7 shows RNA analysis of the effect of 1/244 DI RNA on its own RNA levels in the presence or absence of segment 1-GFP. Northern blot analysis of levels of RNA transcribed from 1/244 DI RNA in the presence of 1.0 µg segment 1-GFP (FIG. 7A) or in the absence of any other genome RNA (FIG. 7C) was carried out as described for FIG. 4. The faint band indicated by(*) is the extension product from the pcDNAPB2 expression plasmid used in the transfection. Quantitation of viral RNA levels from three independent experiments or the range of two replicates for transfections with no added segment 1-GFP plasmid is shown in (FIG. 7B) and (FIG. 7D). The error bars represent the standard error of the mean (FIG. 7B) or range (FIG. 7D). vRNA (■), positive-sense RNA(cRNA+mRNA) (▲).

FIG. 9 shows representations of 244DI RNA.

FIG. 10 shows RNA analysis of cells infected with 244 DI virus. FIG. 10A shows a northern blot of RNA extracted from cells infected with 244 DI virus to detect positive sense influenza RNA transcribed from genome segment 1. Lane I contains total cellular RNA. Lane 2 contains non-polyadenylated RNA. Lane 3 contains polyadenylated mRNA The positions of size markers (nt) are indicated. FIG. 10B shows a northern blot of viral RNAs synthesised by 244 AUG knock-out DI RNA and 244 DI RNA. 48 h after transfection of plasmids, RNA was extracted from cells with Trizol and primer extension analysis carried. Transcription products were resolved on a 6% (w/v) polyacrylamide gel containing 7 M urea in TBE buffer and detected by phosphor imaging. Lane 1 shows a 100 nt size ladder, lane 2 shows RNA made in the presence of 244 DI RNA and lane 3 shows RNA made in the presence of 244 AUG knockout DI RNA, The positions of vRNA and mRNA are indicated. 5S ribosomal RNA was used as a control to confirm similar amounts of total RNA were used.

FIG. 12 shows survival plots of mice inoculated with influenza by treatment with 244 AUG knock-out DI virus or 244 DI virus (1 µg each). Mice were inoculated intranasally with A/WSN alone (10 LD50, 1000 ffu), A/WSN+244 AUG knock-out DI virus, A/WSN+244 DI virus, A/WSN+inactivated 244 AUG knock-out DI virus, A/WSN+inactivated 244 DI virus, or saline alone (FIG. 12A and FIG. 12B). Three weeks after infection mice were challenged with a high dose of A/WSN (10,000 $LD_{50}$) to determine their immune status (FIG. 12C and FIG. 12D). In FIG. 12A, 244 DI+A/WSN, knock-out DI only, 244 DI only, and mock are all hidden under knock-out DI+A/WSN with a clinical score of 1.

DETAILED DESCRIPTION OF THE INVENTION

Figure 1:
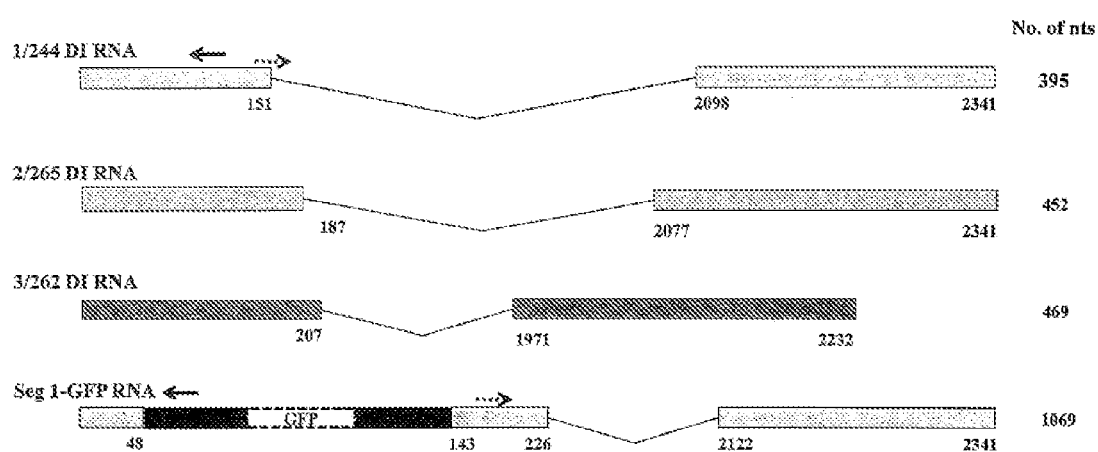
FIG. 1 shows a schematic diagram of influenza DI RNA 1/244 and other RNAs expressed from plasmids. Numbers indicate the nucleotide positions of the various breakpoints in the deleted genome RNAs used in the study (positive-sense, 5' to 3'). Solid arrows indicate the primers used in the primer extension assays for cRNA and mRNA analyses and dashed arrows indicate primers used for vRNA analyses. The black box in segment 1-GFP RNA indicates the position of the reporter GFP gene.

The invention has identified that the effectiveness of a DI influenza A virus to interfere with virus replication can be attributed to the ability of the DI virus RNA to interfere with production of RNA from each of segments 1, 2 and 3 of influenza A virus. Accordingly, the present invention provides methods for identifying DI viruses that are effective as antiviral agents. Thus, the present invention provides a method to identify an antiviral agent by determining whether the defective interfering influenza RNA can interfere with the production of RNA from each of segments 1, 2 and 3 of influenza A virus. A defective interfering influenza virus RNA which is able to interfere with the production of RNA from each of segments 1, 2 and 3 is identified for incorporation in an antiviral agent.

The methods of the present invention can be conducted using any suitable format for the assay which allows for the analysis of the production of RNA from each of segments 1, 2 and 3 of influenza A virus. In accordance with the methods of the present invention, the assays can be conducted in a single assay to monitor for production of RNA from each of segments 1, 2 and 3. Alternatively, multiple assays can be conducted to monitor RNA production from each of segments 1, 2 and 3 separately, or in any combination thereof. For example, the assays can comprise a first assay to monitor for production of RNA from segments 1 and 2 with a separate assay being conducted to monitor RNA production from segment 3. Similarly, production of RNA from segments 2 and 3 can be assayed together, with production of RNA from segment 1 being assayed separately, or production of RNA from segments 1 and 3 can be assayed together, with production of RNA from segment 2 being assayed separately. Typically, a cell is transfected with one or more plasmids that express vRNA from the segments to be analysed, for example using plasmids that express vRNA from segments 1, 2 and 3.

The assays are conducted in the presence of the relevant viral and/or host cell machinery to allow production of RNA from segments 1, 2 and 3. Typically, the methods of the present invention are carried out using a host cell. The host cell is provided with the components necessary to allow viral RNA synthesis. Typically, this can be achieved by transfecting the cell with suitable vectors or plasmids expressing the influenza A polymerase proteins and virus nucleoprotein, and in particular, PB 1, PB2, PA and NP proteins of influenza A. As described above, the cell is typically transfected with additional plasmids expressing vRNA from segments 1, 2 and 3.

Where the structural proteins of influenza A are not encoded or provided, virus particles will not be produced. However, levels of production of RNA from the segments can readily be monitored. This can be done through direct detection of vRNA, cRNA or mRNA associated with each segment. Alternatively, reporter constructs can be provided, for example, encoding negative-sense target RNA can be provided such as a segment-reporter gene construct, encoding a reporter such as green fluorescent protein. Where segments 1, 2 and 3 are assessed in combination such that two or more segments are monitored at the same time, and reporter genes are used, preferably, different reporter genes are used for each segment. Where reporter genes are used, the assays comprise monitoring for expression of the reporter gene. A reduction in reporter gene expression, for example demonstrated by a reduction in fluorescence indicates that production of RNA from the segment-reporter construct has been reduced.

Defective interfering virus RNA for analysis in the assays of the present invention are typically defective interfering virus RNA derived from influenza A. Typically, the DI virus RNA is derived from segment 1, 2 or 3 of influenza A. In one aspect of the present invention, DI virus RNA is introduced into the cells, for example by providing a vector or plasmid encoding DI virus RNA. In an alternative aspect, the assay can be conducted by infecting the cells with DI virus particles. In preferred aspects of the present invention, the DI viruses assayed in accordance with the present invention are cloned DI viruses. Alternatively the method may be used to assay a heterogeneous population of DI viruses, to identify pool(s) containing DI viruses of interest, for subsequent cloning and analysis.

References to inhibition typically refer to at least 10% reduction in production of viral RNA, cRNA or mRNA from each segment, typically at least 20%, 30%, 40% or 50% reduction in viral RNA, cRNA or mRNA production, preferably at least 60%, 70%, 80% or 90%, preferably at least 95%, 97%, 98% or 99% reduction in viral RNA, cRNA or mRNA production. Defective interfering virus RNA showing the highest levels of inhibition of viral synthesis are most preferably used as antiviral agents.

In accordance with another aspect of the present invention, there is provided a defective interfering virus for use as an antiviral agent. The defective interfering virus RNAs of the present invention are derived from influenza A. The defective interfering influenza A RNA may be derived from segment 1, 2 or 3. SEQ ID NOs: 2, 3 and 4 set out the sequences of influenza A virus segment 1 for strains A/Puerto Rico/8/34(H1N1), A/New York/463/2005(H3N2) and A/Netherlands/178/1995(H3N2) respectively. SEQ ID NOs 5, 6 and 7 represent influenza A virus segment 2 of A/Puerto Rico/8/34(H1N1), A/New York/463/2005(H3N2) and A/Netherlands/178/1995(H3N2) respectively. SEQ ID NOs: 8, 9 and 10 represent sequences of influenza A virus segment 3 of A/Puerto Rico/8/34(H1N1), A/New York/463/2005(H3N2) and A/Netherlands/178/1995(H3N2) respectively. In all cases, these sequences are presented in the positive (antigenome sense) from 5' to 3'. The sequences are also represented as DNA.

The sequences of SEQ ID NOs: 2 to 10 provide representative sequences for segments 1, 2 and 3 that can be used to produce the DI RNA in accordance with the present invention. Deletions are introduced into the segments as discussed in more detail above. There is a high degree of sequence identity between the segments of each strain. Segment 1, 2 or 3 from any influenza A strain can be used to design and produce a DI virus. Segment 1 for use in accordance with the present invention to produce a DI virus may have a variant sequence which has at least 80%, 85%, 90% or 95% homology to SEQ ID NO: 2, 3 or 4 based on nucleotide identity over the entire sequence. A segment 2 for use in accordance with the present invention to produce a DI virus may have at least 80%, 85%, 90% or 95% homology to SEQ ID NO: 5, 6 or 7 based on nucleotide identity over the entire sequence. A segment 3 for use in accordance with the present invention to produce a DI virus may have at least 80%, 85%, 90% or 95% homology to SEQ ID NO: 8, 9 or 10 based on nucleotide identity over the entire sequence.

Standard methods in the art may be used to determine homology. For example the UWGCG Package provides the BESTFIT program which can be used to calculate homology, for example used on its default settings (Devereux et al. (1984) *Nucleic Acids* Research 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F. et al. (1990) J Mol Biol 215: 403-10. Software for performing BLAST analyses is publicly available through the National Center for Biotechnology Information (ncbi.nlm.nih.gov). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al., supra). These initial neighbourhood word hits act as seeds for initiating searches to find HSP's containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, $M=5$, $N=4$, and a comparison of both strands.

The BLAST algorithm performs a statistical analysis of the similarity between two sequences; see e.g., Karlin and Altschul (1993) *Proc. Natl. Acad. Sci.* USA 90: 5873-5787. One measure of similarity provided by the BLAST algorithm is the smallest sum probability (P(N)), which provides an indication of the probability by which a match between two amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The defective interfering influenza virus RNA comprises sequences from segment 1, 2 or 3 comprising at least a portion of the 5' region and a portion of 3' region of the segment, and having one or more deletions in the central portion of the segment. The sequences in the 5' end and 3' end of the segment are preferably intact, that is represent contiguous sequences from the 5' and 3' ends of the segment. The regions from the 5' end and 3' end are selected to retain cis-acting signals required for replication and packaging into virus particles. Typically, the defective interfering virus RNA will include at least 100 nucleotides up to 500 nucleotides in length from the 5' end of the segment, preferably up to 400 nucleotides in length, preferably up to 300 nucleotides in length, preferably up to 250 nucleotides in length, such as between 100 to 250 nucleotides in length, 100 to 220 nucleotides in length or 120 to 220 nucleotides in length, say 150 to 220 nucleotides in length from the 5' end of the segment.

Similarly, typically the defective interfering virus RNA comprises the 3' terminus of the segment comprising a contiguous sequence from the 3' terminus, typically comprising at least 100 nucleotides up to 500 nucleotides of the 3' end of the segment, preferably 150 nucleotides up to 400 nucleotides, such as 150 nucleotides up to 280 nucleotides of the 3' end of the segment. The deletion comprises deletion of a central portion of the segment, typically up to 2,000 nucleotides in length, typically at least 1,000 nucleotides in length, at least 1,500 nucleotides in length, 1,800 nucleotides in length, 2,000 nucleotides in length.

Thus, the defective interfering virus RNA according to the present invention typically has a total length of between 300 nucleotides and 600 nucleotides, typically 300 nucleotides up to 500 nucleotides, preferably between 380 nucleotides up to 480 nucleotides in length.

The defective interfering viruses in accordance with the present invention are characterised by their ability to interfere with production of RNA from segments 1, 2 and 3 of influenza A virus. Assays for the activity of the virus can be conducted in accordance with the methods described herein. Typically, the defective interfering virus RNA for incorporation into the virus particle is produced by recombinant means. Standard recombinant techniques can be used to introduce deletions into segments 1, 2 or 3 RNA Alternatively, the defective interfering virus of the present application may be cloned or recombinant viruses, for example, to provide a cloned or recombinant preparation based on a naturally occurring defective interfering virus. For example, samples can be taken from infected individuals, animals or to identify cells for the presence of defective interfering virus particles. Such DI viruses can be screened to identify the presence of defective interfering viruses which inhibit viral replication from each of segments 1, 2 and 3. The DI RNA of the viruses are then isolated and cloned by recombinant techniques to provide a cloned preparation of defective interfering virus having the characteristics as now claimed.

The DI virus RNA as described herein can be incorporated into a viral particle in order to produce a DI virus for use as an antiviral agent. Such virus particles can be produced by transfecting a cell with a plasmid or vector expressing the DI virus RNA and plasmids or vectors which in combination express RNA segments 1 to 8 of an influenza A RNA and protein expression can be used in order to generate viral particles comprising the DI virus RNA Methods of generating cloned DI influenza virus are described for example in WO2007/135420.

In accordance with a preferred aspect of the present invention, the DI virus of the present application is not 1/244.

A DI virus identified as an antiviral agent, or a DI virus in accordance with the present invention may be used in a method to treat a viral infection in a subject, and in particular to treat influenza A infection in a subject. The invention also provides a method of preventing or treating influenza A infection in a subject, comprising administering to the subject an effective amount of a DI virus identified in accordance with the invention, or an DI virus of the invention as described above.

The invention also provides a DI virus identified in accordance with the invention, or of the invention for use in a method of preventing or treating influenza A infection. The invention further provides use of a DI virus identified in accordance with the invention, or of the invention in the manufacture of a medicament for preventing or treating influenza A infection.

DI viruses derived from influenza A have also been demonstrated to be effective in the treatment of virus infections caused by other viruses, in particular, respiratory virus infections. Thus, a DI virus in accordance with the present invention may also be used for the treatment of other respiratory virus infections, including virus infections caused by viruses of the paramyxoviridae, such as pneumovirus or metanpeurovirus, and viruses caused by viruses of the orthomyoviridae. Examples of respiratory viruses that can be treated in accordance with the present invention include human respiratory syncytial virus, human metapneumovirus, influenza B or influenza C virus.

Typically, the individual is human. The subject is typically a patient, but may also be an individual at risk of infection.

The DI virus of the invention may be used for treating influenza A infection. In the case of treating, the subject typically has an influenza A infection, i.e. has been diagnosed as having an influenza A infection, or is suspected as having an influenza A infection, i.e. shows the symptoms of an influenza A infection. The individual may also be at risk of infection, and the DI virus is used prophylactically to prevent or treat infection by administration up to 2 weeks, typically up to 1 week before exposure to influenza A The subject is typically symptomatic but may also be asymptomatic. As used herein, the term "treating" includes any of following: the prevention of an influenza A infection or of one or more symptoms associated with an influenza A infection; a reduction or prevention of the development or progression of the influenza A infection or symptoms; and the reduction or elimination of an existing influenza A infection or symptoms.

Therapy and prevention includes, but is not limited to, alleviating, reducing, curing or at least partially arresting symptoms and/or complications resulting from or associated with an influenza A infection. When provided therapeutically, the therapy is typically provided at or shortly after the onset of a symptom of an influenza A infection. Such therapeutic administration is typically to prevent or ameliorate the progression of, or a symptom of the infection or to reduce the severity of such a symptom or infection. When provided prophylactically, the treatment is typically provided before the onset of a symptom of an influenza A infection. Such prophylactic administration is typically to prevent the onset of symptoms of the infection. The DI viruses identified in accordance with the present invention or of the present invention may be administered to treat or prevent infection, before an individual is infected, but where the individual is suspected or likely to come into contact with influenza A virus. For example, the DI virus of the present invention may be administered 1 day, 3 days, 1 week or up to 2 weeks before exposure to influenza A.

Specific routes, dosages and methods of administration of the DI virus identified in accordance with the invention, or of the invention may be routinely determined by the medical practitioner. These are discussed in more detail below. Typically, a therapeutically effective or a prophylactically effective amount of the DI virus of the invention is administered to the subject. A prophylactically effective amount is an amount which prevents the influenza A infection and/or the onset of one or more symptoms of the influenza A infection. A therapeutically effective amount is an amount effective to ameliorate one or more symptoms of the influenza A infection. A therapeutically effective amount preferably abolishes one or more symptoms of the disease. Typically, such an amount reduces the influenza A infection or viral titre in the subject.

The DI virus of the invention may be used in combination with one or more other therapies intended to treat the same subject. By a combination is meant that the therapies may be administered simultaneously, in a combined or separate form, to a subject. The therapies may be administered separately or sequentially to a subject as part of the same therapeutic or prophylactic regimen. For example, the DI virus of the invention may be used in combination with another therapy intended to inhibit influenza A infection or manage a symptom thereof. The other therapy may be a general therapy aimed at treating or improving the condition of a subject with an influenza A infection.

The DI virus identified in accordance with the invention or of the invention can be administered to the subject by any suitable means. Typically the DI virus is administered to the respiratory airways, typically by intranasal or intrabuccal administration, inhalation or instillation.

The DI virus of the invention can be formulated into pharmaceutical compositions. These compositions may comprise, in addition to one of the above DI viruses, a pharmaceutically acceptable carrier or diluent. Such compositions may also comprise other excipients, buffers, stabilisers or other materials well known to those skilled in the art. Such materials should be non-toxic and should not interfere with the efficacy of the DI virus. The precise nature of the carrier or diluent may depend on the route of administration, e.g. oral, intravenous, cutaneous or subcutaneous, nasal, intramuscular, intraperitoneal routes.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the pharmaceutical composition is lyophilised, the lyophilised material may be reconstituted prior to administration, e.g. a suspension. Reconstitution is preferably effected in water.

Typically the formulations are suitable for intranasal delivery and may be provided in the form of a nasal spray, nasal drops, gel or powder.

An effective amount, such as a therapeutically or prophylactically effective amount, of the DI virus is administered. The dose may be determined according to various parameters, especially according to the DI virus used; the age, weight and condition of the subject to be treated; the route of administration; and the required regimen. Again, a physician will be able to determine the required route of administration and dosage for any particular subject.

In another aspect of the present invention, a DI virus is provided in which the DI virus RNA is not able to produce a protein. Typically, this is achieved by mutating DI virus RNA to remove signalling sequences required for protein expression. In one aspect of the present invention, this is done by deletion or substitution of one or more AUG initiation codons. For example, the initiation codon may be mutated at one or more positions. In one aspect, we describe mutation of one or more initiation codons to AUC, and typically all initiation codons are mutated to AUC.

The DI virus RNA of the invention may be a known DI virus. In one preferred aspect of the present invention, with DI virus RNA is 1/244 which incorporates a mutation of AUG initiation codons. The DI virus may include one or more mutations to mutate one, more than one or all AUG initiation codons in the DI virus. In the case of 244 DI RNA, mutations are introduced in the AUG initiation codons present at positions 28 to 30, 58 to 60 and 109 to 111. Suitable mutations include mutation of G to C for example at positions 30, 60 and 111 of 244 DI RNA Similar mutations can be incorporated in other DI RNA, particularly, DI RNA derived from influenza A virus. Such DI RNA can be that as described above. In particular, the defective interfering influenza A RNA may be derived from segment 1, 2 or 3. SEQ ID NOs: 2, 3 and 4 set out the sequences of influenza A virus segment 1 for strains A/Puerto Rico/8/34(H1N1), A/New York/463/2005(H3N2) and A/Netherlands/1 78/1995(H3N2) respectively. SEQ ID NOs 5, 6 and 7 represent influenza A virus segment 2 of A/Puerto Rico/8/34(H1N1), A/New York/463/2005(H3N2) and A/Netherlands/1 78/1995(H3N2) respectively. SEQ ID NOs: 8, 9 and 10 represent sequences of influenza A virus segment 3 of A/Puerto Rico/8/34(H1N1), A/New York/463/2005(H3N2) and A/Netherlands/178/1995(H3N2) respectively. In all cases, these sequences are presented in the positive (antigenome sense) from 5' to 3'. The sequences are also represented as DNA.

The sequences of SEQ ID NOs: 2 to 10 provide representative sequences for segments 1, 2 and 3 that can be used to produce the DI RNA in accordance with the present invention. Deletions are introduced into the segments as discussed in more detail above. There is a high degree of sequence identity between the segments of each strain. Segment 1, 2 or 3 from any influenza A strain can be used to design and produce a DI virus. Segment 1 for use in accordance with the present invention to produce a DI virus may have a variant sequence which has at least 80%, 85%, 90% or 95% homology to SEQ ID NO: 2, 3 or 4 based on nucleotide identity over the entire sequence. A segment 2 for use in accordance with the present invention to produce a DI virus may have at least 80%, 85%, 90% or 95% homology to SEQ ID NO: 5, 6 or 7 based on nucleotide identity over the entire sequence. A segment 3 for use in accordance with the present invention to produce a DI virus may have at least 80%, 85%, 90% or 95% homology to SEQ ID NO: 8, 9 or 10 based on nucleotide identity over the entire sequence.

Standard methods in the art may be used to determine homology. For example the UWGCG Package provides the BESTFIT program which can be used to calculate homology, for example used on its default settings (Devereux et al. (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (199 3) J Mol Evol 36:290-300; Altschul, S. F et al. (1990) J Mol Biol 2 15: 403-10.

Software for performing BLAST analyses is publicly available through the National Center for Biotechnology Information (ncbi.nlm.nih.gov). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al., supra). These initial neighbourhood word hits act as seeds for initiating searches to find HSP's containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.* USA 90: 5873-5787. One measure of similarity provided by the BLAST algorithm is the smallest sum probability (P(N)), which provides an indication of the probability by which a match between two amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The defective interfering influenza virus RNA comprises sequences from segment 1, 2 or 3 comprising at least a portion of the 5' region and a portion of 3' region of the segment, and having one or more deletions in the central portion of the segment. The sequences in the 5' end and 3' end of the segment are preferably intact, that is represent contiguous sequences from the 5' and 3' ends of the segment. The regions from the 5' end and 3' end are selected to retain cis-acting signals required for replication and packaging into virus particles. Typically, the defective interfering virus RNA will include at least 100 nucleotides up to 500 nucleotides in length from the 5' end of the segment, preferably up to 400 nucleotides in length, preferably up to 300 nucleotides in length, preferably up to 250 nucleotides in length, such as between 100 to 250 nucleotides in length, 100 to 220 nucleotides in length or 120 to 220 nucleotides in length, say 150 to 220 nucleotides in length from the 5' end of the segment.

Similarly, typically the defective interfering virus RNA comprises the 3' terminus of the segment comprising a contiguous sequence from the 3' terminus, typically comprising at least 100 nucleotides up to 500 nucleotides of the 3' end of the segment, preferably 150 nucleotides up to 400 nucleotides, such as 150 nucleotides up to 280 nucleotides of the 3' end of the segment. The deletion comprises deletion of a central portion of the segment, typically up to 2,000 nucleotides in length, typically at least 1,000 nucleotides in length, at least 1,500 nucleotides in length, 1,800 nucleotides in length, 2,000 nucleotides in length.

Thus, the defective interfering virus RNA according to the present invention typically has a total length of between 300 nucleotides and 600 nucleotides, typically 300 nucleotides up to 500 nucleotides, preferably between 380 nucleotides up to 480 nucleotides in length.

Typically, the defective interfering virus RNA for incorporation into the virus particle is produced by recombinant means. Standard recombinant techniques can be used to introduce deletions into segments 1, 2 or 3 RNA, together with further mutations to one or more of the initiation codons as described above.

The DI virus RNA as described herein can be incorporated into a viral particle in order to produce a DI virus for use as an antiviral agent. Such virus particles can be produced by transfecting a cell with a plasmid or vector expressing the DI virus RNA and plasmids or vectors which in combination express RNA segments 1 to 8 of an influenza A RNA and protein expression can be used in order to generate viral particles comprising the DI virus RNA A DI virus in accordance with this aspect of the present invention may be used in a method to treat a viral infection in a subject, for example to treat influenza A infection in a subject. The invention also provides a method of preventing or treating influenza A infection in a subject, comprising administering to the subject an effective amount of a DI virus of the invention as described herein. The DI virus in accordance with this aspect of the invention may also be used to treat other viral infections.

The invention also provides a DI virus of this aspect of the invention for use in a method of preventing or treating influenza A infection. The invention further provides use of a DI virus of this aspect of the invention in the manufacture of a medicament for preventing or treating influenza A infection.

DI viruses derived from influenza A have also been demonstrated to be effective in the treatment of virus infections caused by other viruses, in particular, respiratory virus infections. Thus, a DI virus in accordance with the present invention may also be used for the treatment of other respiratory virus infections, including virus infections caused by viruses of the paramyxoviridae, such as pneumovirus or metanpeurovirus, and viruses caused by viruses of the orthomyoviridae. Examples of respiratory viruses that can be treated in accordance with the present invention include human respiratory syncytial virus, human metapneumovirus, influenza B or influenza C virus.

Typically, the individual is human. The subject is typically a patient, but may also be an individual at risk of infection.

The DI virus of the invention may be used for treating influenza A infection. In the case of treating, the subject typically has an influenza A infection, i.e. has been diagnosed as having an influenza A infection, or is suspected as having an influenza A infection, i.e. shows the symptoms of an influenza A infection. The individual may also be at risk of infection, and the DI virus is used prophylactically to prevent or treat infection by administration up to 2 weeks, typically up to 1 week before exposure to influenza A The subject is typically symptomatic but may also be asymptomatic. As used herein, the term "treating" includes any of following: the prevention of an influenza A infection or of one or more symptoms associated with an influenza A infection; a reduction or prevention of the development or progression of the influenza A infection or symptoms; and the reduction or elimination of an existing influenza A infection or symptoms.

Therapy and prevention includes, but is not limited to, alleviating, reducing, curing or at least partially arresting symptoms and/or complications resulting from or associated with an influenza A infection. When provided therapeutically, the therapy is typically provided at or shortly after the onset of a symptom of an influenza A infection. Such therapeutic administration is typically to prevent or ameliorate the progression of, or a symptom of the infection or to reduce the severity of such a symptom or infection. When provided prophylactically, the treatment is typically provided before the onset of a symptom of an influenza A infection. Such prophylactic administration is typically to prevent the onset of symptoms of the infection. The DI viruses identified in accordance with the present invention or of the present invention may be administered to treat or prevent infection, before an individual is infected, but where the individual is suspected or likely to come into contact with influenza A virus. For example, the DI virus of the present invention may be administered 1 day, 3 days, 1 week or up to 2 weeks before exposure to influenza A.

Specific routes, dosages and methods of administration of the DI virus identified in accordance with the invention, or of the invention may be routinely determined by the medical practitioner. These are discussed in more detail below. Typically, a therapeutically effective or a prophylactically effective amount of the DI virus of the invention is administered to the subject. A prophylactically effective amount is an amount which prevents the influenza A infection and/or the onset of one or more symptoms of the influenza A infection. A therapeutically effective amount is an amount effective to ameliorate one or more symptoms of the influenza A infection. A therapeutically effective amount preferably abolishes one or more symptoms of the disease. Typically, such an amount reduces the influenza A infection or viral titre in the subject.

The DI virus of the invention may be used in combination with one or more other therapies intended to treat the same subject. By a combination is meant that the therapies may be administered simultaneously, in a combined or separate form, to a subject. The therapies may be administered separately or sequentially to a subject as part of the same therapeutic or prophylactic regimen. For example, the DI virus of the invention may be used in combination with another therapy intended to inhibit influenza A infection or manage a symptom thereof. The other therapy may be a general therapy aimed at treating or improving the condition of a subject with an influenza A infection.

The DI virus of the invention can be administered to the subject by any suitable means. Typically the DI virus is administered to the respiratory airways, typically by intranasal or intrabuccal administration, inhalation or instillation.

The DI virus of the invention can be formulated into pharmaceutical compositions. These compositions may comprise, in addition to one of the above DI viruses, a pharmaceutically acceptable carrier or diluent. Such compositions may also comprise other excipients, buffers, stabilisers or other materials well known to those skilled in the art. Such materials should be non-toxic and should not interfere with the efficacy of the DI virus. The precise nature of the carrier or diluent may depend on the route of administration, e.g. oral, intravenous, cutaneous or subcutaneous, nasal, intramuscular, intraperitoneal routes.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the pharmaceutical composition is lyophilised, the lyophilised material may be reconstituted prior to administration, e.g. a suspension. Reconstitution is preferably effected in water.

Typically the formulations are suitable for intranasal delivery and may be provided in the form of a nasal spray, nasal drops, gel or powder. An effective amount, such as a therapeutically or prophylactically effective amount, of the DI virus is administered. The dose may be determined according to various parameters, especially according to the DI virus used; the age, weight and condition of the subject to be treated; the route of administration; and the required regimen. Again, a physician will be able to determine the required route of administration and dosage for any particular subject.

EXAMPLES

Example 1—DI RNA Inhibits RNA Production from Segments 1, 2 and 3

Materials and Methods
Plasmids

The plasmids encoding the 8 gene segments of the A/WSN strain of A/WS/33 and plasmids expressing the polymerase proteins and NP (Neumann et al. 1999), and the vector expressing 1/244 DI RNA (FIG. 1) were as previously described (Duhaut and Dimmock 2002; Dimmock et al. 2008). 1/244 RNA comprises 395 nt and was derived from segment 1 of A/Puerto Rico/8/34 (HIND. The segment 1 target, segment 1-GFP, was created by amplifying the GFP ORF by PCR from pEGFP-N1(Clontech) using primers 5'ATGGTCTCTACTGATGGTGAGCAAGGGCGAG (SEQ ID NO: 11) and 5'ATGAAGACAATCTCT-TACTTGTACAGCTCGTCCA (SEQ ID NO: 12). The product was inserted between the BpiI and Eco31I sites of pPolI-220 (Duhaut and Dimmock 2000) such that the GFP ORF is in-frame with the PB2 ORF, giving plasmid seg 1-GFP which expresses segment 1-GFP RNA(FIG. 1). The GFP reporter retains the exact 5' (220 nt) and 3' (48 nt) terminus of segment 1 and is cognate for 1/244 DI RNA A segment 2 DI(2/265; comprising 452 nt in total with 265 nt from the 5' end and 187 nt from the 3' end of the negative-sense cognate RNA) was isolated from a DI A/equine/Newmarket/7339/79 (H3N8) virus preparation (FIG. 1) (Mann et al. 2006) by RT-PCR amplification, and subsequently cloned into a pPolI-SapIT expression vector(Subbarao et al. 2003). A segment 3 DI RNA(3/262; comprising 469 nt in total with 262 nt from the 5' end and 207 nt from 3' end of the negative-sense cognate RNA) was isolated from a DI A/WSN preparation, and was amplified and cloned as above (FIG. 1). The DI RNAs encoded by the various plasmids retain the exact nucleotide sequences from the termini of the genome segments of the viruses from which they were derived and do not contain any mutations in positions known to have an effect on replication or packaging.

Transfection

Human 293T cells were transfected as previously described (Dimmock et al. 2008). Briefly, for northern blot analysis, a well of 70% confluent 293T cells in a 12-well plate was transfected using TransIT LT1 transfection reagent (Mirus) with 8 PolI expression plasmids encoding viral sense RNA and cDNA plasmids for expression of PB2, PB1, PA and NP proteins, with or without pPolI-244. The transfected cells were then incubated at 37° C. overnight before co-culture with MDCK cells in a 25 cm² flask. Total cellular RNA was extracted with 2 ml Trizol reagent per sample (Invitrogen) on days 1, 2 and 3 after co-culture while tissue culture fluid was collected for virus titration and RNA extraction. Virions were purified by ultracentrifugation. RNA was extracted with phenol/chloroform, and then ethanol precipitated. For transfections, each well of a 6 well plate containing 70% confluent 293T cells was transfected with 1 µg each of the PB2, PB1, PA and NP cDNA expression plasmids plus various amounts of a DI plasmid or pPolI-NA together with 1 µg of target plasmid. After two days' incubation at 37° C. the supernatant was discarded and RNA was extracted with Trizol.

Infectivity Assay

MDCK cell monolayers in 96-well plates were infected with supernatant containing rescued A/WSN as described previously (Scott et al. 2011). After 1 hour for attachment of virus, the monolayer was washed with PBS, and incubated in maintenance medium overnight at 33° C. Cells were then fixed with 4% (v/v) formaldehyde, washed and blocked with 5% (w/v) milk powder in PBS. The infected cells were probed with a monoclonal antibody specific for the HA of A/WSN in PBS containing 0.1% Tween 20. After washing, goat anti-mouse IgG alkaline phosphatase conjugate (Sigma) in TBS containing 0.1% Tween 20 was added, and infected cells detected with nitrotetrazolium blue chloride/BCIP (Sigma) in Tris-buffered magnesium chloride and sodium chloride (0.1 M, pH 9.5). The infectivity titre was determined by counting at least 50 positively stained cells (foci) at an appropriate dilution in each of the triplicate wells. The mean number of counts was determined to give a titre in focus-forming units (f.f.u.) ml$^{-1}$.

Primer Extension

Total cellular RNA was extracted from cells with Trizol at 48 h post-transfection and used for primer extension analysis (Rehwinkel et al. 2010). Two µg of total RNA was mixed with [$^{32}$P]5'-end labelled primers and dNTP in a total volume of 13 µl. The mixture was heated at 65° C. for 5 min and placed on ice for 1 min. 2× first Strand Buffer, 20 mM DTT, and 100 U SuperScript III reverse transcriptase (Invitrogen) were added and further incubated at 55° C. for 1 h. The reaction was terminated by heating at 95° C. for 5 min with gel loading dye II (Ambion). The transcription products were resolved on a 6% (w/v) polyacrylamide gel containing 7 M urea in TBE buffer and detected by phosphor imaging. The primers used are shown in Table 1 and the positions of these on the various target RNAs are demonstrated in FIG. 1.

TABLE 1

Sequences of the primers used in this study. The primers containing mixed nucleotides were designed for detection of both A/PR8 and A/WSN-derived RNAs. Primers indicated with an asterisk were taken from (Rehwinkel et al. 2010).

| Target RNA | Primer specificity | Primer sequence |
|---|---|---|
| Segment 1-GFP | c/mRNA | GGACACGCTGAACTTGTGG (SEQ ID NO: 15) |
| | vRNA | AGATAAGAGGATAATGGAAATG (SEQ ID NO: 16) |
| DI 1/244 | c/mRNA | ATATGGTCCACKGTGGTTTTTG (SEQ ID NO: 17) |
| | vRNA | GGAGAAGACTGAGGGGATTC (SEQ ID NO: 18) |
| Segment 2 (PB1) | c/mRNA* | TCCATGGTGTATCCTGTTCC (SEQ ID NO: 19) |
| | vRNA* | TGATTTCGAATCTGGAAGGA (SEQ ID NO: 20) |
| Segment 3 (PA) | c/mRNA* | TGAGTGCATATTGCTGCAAAT (SEQ ID NO: 21) |
| | vRNA* | TTCTTATCGTTCAGGCTCTT (SEQ ID NO: 22) |
| Segment 6 (NA) | c/mRNA* | TCCAGTATGGTTTTGAYTTCCR (SEQ ID NO: 23) |
| | vRNA* | TGGACTAGTGSGAGCATSAT (SEQ ID NO: 24) |
| 5S rRNA* | | TCCCAGGCGGTCTCCCATCC (SEQ ID NO: 25) |

Northern Blotting

Ten µg of total cellular RNA or 50% of the yield of purified virion RNA from each sample was used for glyoxal-agarose gel electrophoresis. The RNA was transferred onto Hybond-N membrane (GE Healthcare) overnight using 20×SSC. The membrane was then baked at 80° C. for 2 h and hybridized with digoxigenin (DIG)-labelled probes overnight. The full-length positive-sense DIG-labelled segment 1, segment 2 and segment 7 probes were transcribed in vitro in the presence of DIG-UTP (Roche) from PCR products containing a T7 promoter. The Roche system with a digoxigenin-specific alkaline phosphatase conjugated FAb antibody fragment and the chemiluminescent CSPD substrate was used for detection. Blots were exposed to Fuji X-ray film until the desired density was achieved and bands were quantified by densitometry using ImageJ (NIH).

Quantitation of GFP-Expressing Cells 293T cells were transfected with the segment 1-GFP RNA expressing plasmid, plasmids expressing PB1, PB2, PA and NP proteins, and increasing amounts of an additional PolI plasmid expressing a DI RNA (1/244, 2/265 and 3/262) or a full-length RNA (segment 4 or 6). At two days post-transfection, the cultures were examined for GFP expression. Digital images of the cell monolayers were taken by phase-contrast and epifluorescence microscopy. Five field fluorescence images were randomly selected and analysed for the proportion of the visualised area expressing GFP using the HCimage software (Hamamatsu). The visualisation detects cells expressing a range of GFP levels to include those that may have been transfected with different levels of the reporter plasmids. A mean was calculated to give the percentage of the GFP positive area per monolayer.

Results

1/244 DI RNA Interferes with Packaging of Segment 1

Figure 2A:
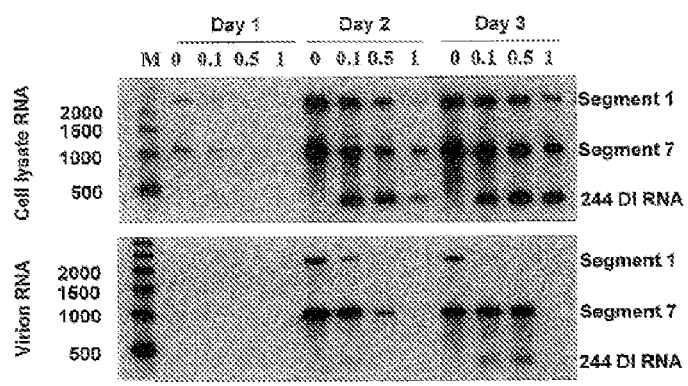
FIG. 2A shows a northern blot of RNA extracted from cell lysates (top panel) and virus particles from supernatants (lower panel) at 1, 2 and 3 days post co-cultivation and analysed with probes specific for segment 1 RNA and 1/244 DI RNA, and for segment 7 vRNA. The sizes of RNA markers are shown on the left and the identity of each RNA species is shown on the right.
Figure 2B:
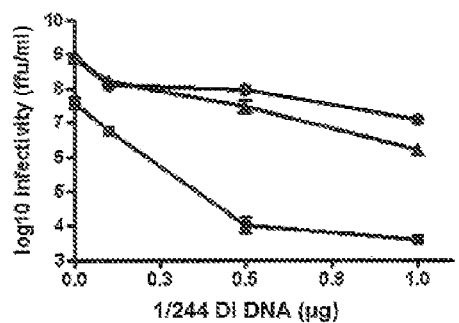
FIG. 2B is a line graph showing A/WSN infectivity in cell supernatants measured by microplaque assay. The infectivities on 1 (■), 2 (▲) and 3 (●) days after co-cultivation are shown. Data show the mean of 2 independent experiments with the bar representing the range.
Figure 2C:
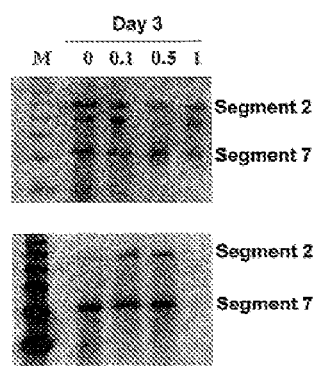
FIG. 2C shows a northern blot analysis of cell lysate RNA and virion RNA extracted on day 3 and analysed with probes specific for segment 2 and segment 7 RNA.
Figure 2D:
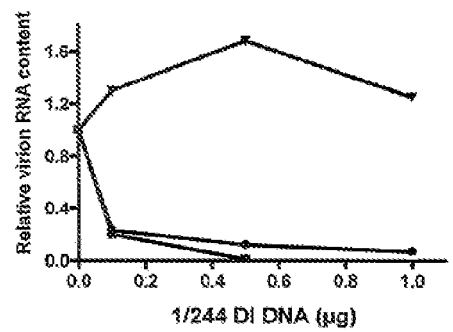
FIG. 2D is a line graph showing a comparison of the ratio of segment 1 RNA in virions: transfected cells on days 2 (■) and 3 (●), and of segment 2 RNA in virions: transfected cells on day 3 (▼). Data were normalized against levels of segment 7 and expressed as a fraction of the virion: cellular RNA ratio in the absence of 1/244 DI RNA.

We have used a plasmid rescue system to generate a preparation of influenza virus in which 1/244 DI RNA was the only DI RNA present (Dimmock et al. 2008). The derivation of DI RNA 1/244 from segment 1 is shown in FIG. 1. This was used to investigate the effect of increasing amounts of 1/244 DI DNA on the levels of segment 1, 2 and 7 vRNAs in infected cells and purified virus particles at days 1-3 post-coculture. It was previously shown that influenza vRNAs are only detectable when all of the virus RNA polymerase components are present, demonstrating that the vRNAs are generated by the virus polymerase (Duhaut and Dimmock 2002). The 1/244 DI RNA (395 nt) was observed only in cultures transfected with the 1/244 plasmid, confirming that no other segment 1 DI RNA sequences were generated during the experiment (FIG. 2A). As the amount of 1/244 DI plasmid DNA in the transfection increased there was a progressive reduction in the level of segment 7 vRNA detected in the cells on each of the three days examined. The reduction in virus infectivity titre observed with increasing 1/244 plasmid on each of the 3 days confirmed that 1/244 DI RNA-mediated interference was taking place (FIG. 2B). As the input of 1/244 DI plasmid increased, the level of segment 1 vRNA within virus particles decreased dramatically, and was undetectable when 1 μg 1/244 plasmid was transfected (FIG. 2A, lower panel). Quantitation showed that in the presence of 1/244 RNA, the ratio of segment 1: segment 7 vRNAs was considerably lower in virions than it was in cell extracts (FIG. 2D). This established that 1/244 DI RNA (derived from segment 1) acts, at least in part, by selectively excluding full-length segment 1 vRNA from progeny virus particles. The segment 2 vRNA content of virions was not reduced in the presence of increasing amounts of transfected 1/244 plasmid (FIG. 2C, FIG. 2D), confirming that inhibition of packaging of segment 1 by 1/244 RNA was specific, and did not extend to other polymerase component-encoding RNA segments.

Segment 1, 2 or 3 DI RNAs Inhibit Gene Expression from Segment 1

Figure 3G:
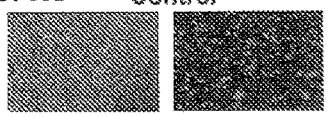
FIG. 3G is a bar graph showing quantitation of fluorescence in cells generated in the presence of transfected plasmids expressing 1/244 RNA (black columns) and segment 6 RNA (white columns). Columns show the mean of 3 independent experiments, and bars are standard errors of the mean. Statistical analyses were done using a two-tailed Student t test and the p values for specific comparisons are shown.
Figure 3G:
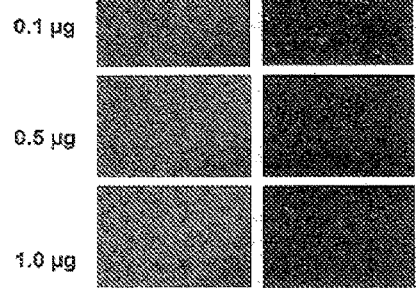
Figure 3G:
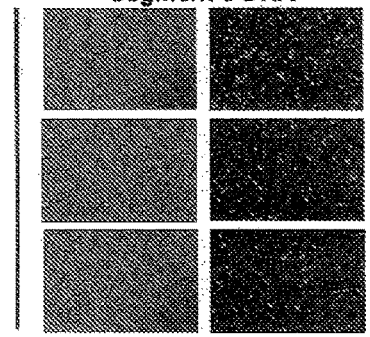
Figure 3G:
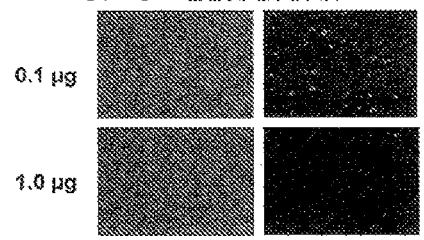
Figure 3G:
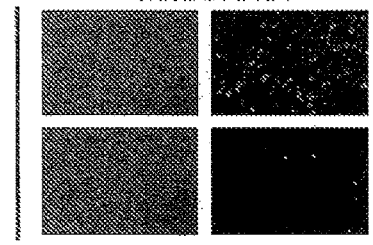
Figure 3G:
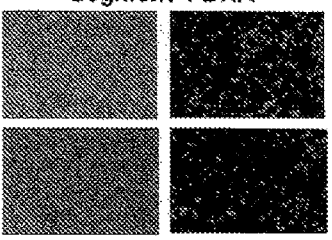
Figure 3G:
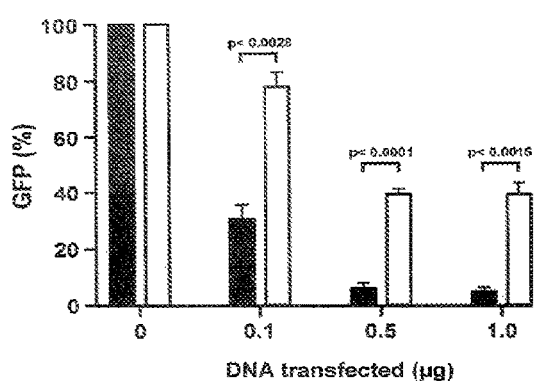

To separate the possible effects of DI RNA on viral RNA synthesis from RNA packaging, we devised a GFP expression assay in which transcription and replication of a GFP-encoding negative-sense target RNA (segment 1-GFP; FIG. 1) were enabled by co-transfection of plasmids expressing PB1, PB2, PA and NP proteins. This system allows viral RNA synthesis but not virus particle formation as plasmids encoding key structural proteins (HA, NA, M1 and M2) were omitted. The effects of co-transfected DI RNA-encoding plasmids were assessed by monitoring GFP fluorescence. In the absence of the plasmid encoding the PB2 protein no GFP expression was detected (data not shown). FIG. 3B shows that the 1/244 DI plasmid strongly inhibited fluorescence in a dose-dependent manner compared with a culture transfected with 1 μg of empty control vector. Inhibition was far less marked when cells were transfected with plasmids that synthesized full-length segment 4 or segment 6 vRNAs. Quantitation showed that 0.1 μg of 1/244 DI plasmid inhibited GFP fluorescence by 70%, whereas approximately 10-fold more of the segment 6 plasmid was required to produce a similar level of inhibition(61-69%) (FIG. 3G). Statistical analysis showed that the inhibitory effect of 1/244 DI RNA was highly significantly different to the effects of segment 6 RNA (FIG. 3G). Thus 1/244 DI RNA strongly inhibits the expression from a segment 1 target RNA Further assays showed that a segment 2-derived DI RNA (2/265) and a segment 3-derived DI RNA (3/262) also strongly inhibited GFP fluorescence from the segment 1-derived target, whereas a full-length segment 4 vRNA, like segment 6 vRNA was only weakly inhibitory (FIG. 3E and FIG. 3F). At the highest concentration of plasmid DNA used (1 μg), segment 4 vRNA reduced segment 1-derived gene expression to 75% of the control level, while 2/265 and 3/262 DI RNAs reduced expression to 2% and 6% of the control, respectively.

1/244 DI RNA Differentially Inhibits Positive Sense RNA Synthesis from Genome Segment 1, 2 and 3 but not Segment 6

Figure 4A:
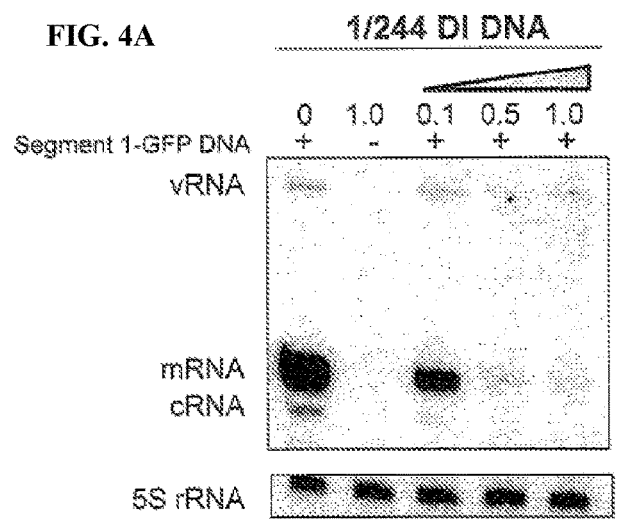
FIG. 4 shows RNA analysis of influenza segment 1-directed RNA synthesis by primer extension in the presence of influenza DI RNAs or segment 6 RNA. Transfections were carried out as described for FIG. 3. Primer extension analysis of viral RNA levels directed by segment 1-GFP in the absence or in the presence of increasing amount of plasmids encoding 1/244 DI RNA (FIG. 4A) or genome segment 6 vRNA (FIG. 4C). 5S rRNA detected from the same RNA preparations is also shown and were used as an internal control. The primer extension products are identified on the left of each panel. Quantitation of viral RNA levels from three independent experiments by phosphorimaging analysis is shown in FIG. 4B and FIG. 4D. The values of band intensities were normalised against the relevant 5S rRNA and are expressed as a percentage of the maximum value for each RNA analysed. Basal levels of vRNA generated from the target plasmid were subtracted from the total. The error bars represent the standard error of the mean of at least 3 replicates. vRNA (■), mRNA(▲) and cRNA(▼).
Figure 4C:
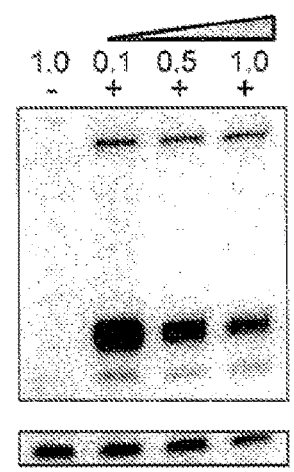

Expression of GFP from the segment 1-GFP PolI plasmid is dependent on transcription of the negative-sense vRNA into mRNA. However, vRNA is also template for cRNA, which in turn acts as template for the production of more vRNA. Influenza virus mRNA has a 5'-extension of approximately 12 nt cleaved from the host mRNA (Palese and Shaw 2007) so the mRNA and cRNA products can be distinguished by size. Using a primer extension assay which detects levels of vRNA, mRNA and cRNA, we identified the stage of target RNA synthesis with which 1/244 DI RNA interferes (FIG. 4A, FIG. 4C). The basal levels of vRNAs synthesised directly from the transfected plasmid DNA were subtracted from the values presented in the data shown in FIG. 4B and FIG. 4D.

Taken together, the data in FIG. 3 and FIG. 4 show that the reduction in the level of segment 1-GFP-encoded mRNA in the presence of increasing amounts of DI RNA was strongly positively correlated with the reduction in GFP fluorescence ($R^2$=0.90; data not shown), confirming that fluorescence was a faithful marker of mRNA synthesis. Quantitation of these data showed that mRNA and cRNA levels were considerably more affected than vRNA in the presence of 0.1 μg to 0.5 μg of 1/244 plasmid DNA (FIG. 4B). Addition of 0.1 μg of 1/244 plasmid DNA reduced mRNA and cRNA levels to 13% and 10% of the control, respectively, while the level of vRNA was only reduced to 61%. However, with 1 μg 1/244 DI RNA, levels of all de novo RNAs synthesised from segment 1 were reduced by >99%. Thus 1/244 DI RNA has a profound effect on all RNAs synthesised from the segment 1 target but differentially affects the levels of positive-strand and negative-strand RNAs.

To control for the specificity of action of the inhibiting RNA, we transfected a segment 6 plasmid (encoding the NA gene) in the place of the DI RNA plasmid.

Figure 4B:
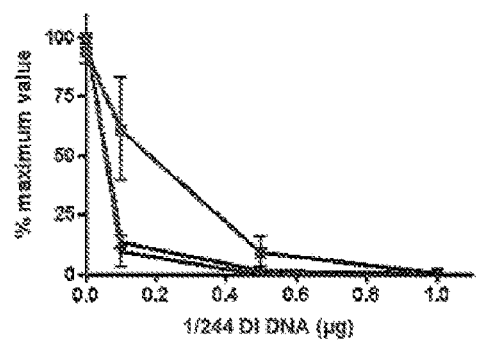
Figure 4D:
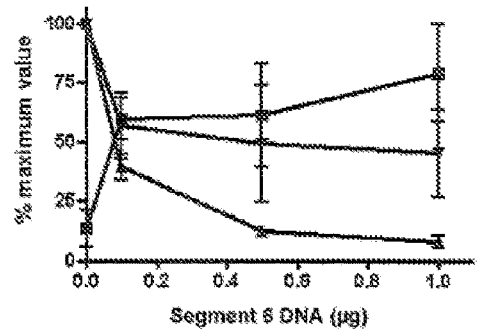

FIG. 4C and FIG. 4D show that segment 6 RNA was significantly less effective at inhibiting mRNA, cRNA and vRNA expression by the segment 1 target than 1/244 RNA This is consistent with the lower level of fluorescence inhibition achieved by the segment 6 RNA (FIG. 3). Thus, 1/244 DI RNA specifically reduced mRNA, cRNA and vRNA levels, but segment 6 did not.

Figure 5A:
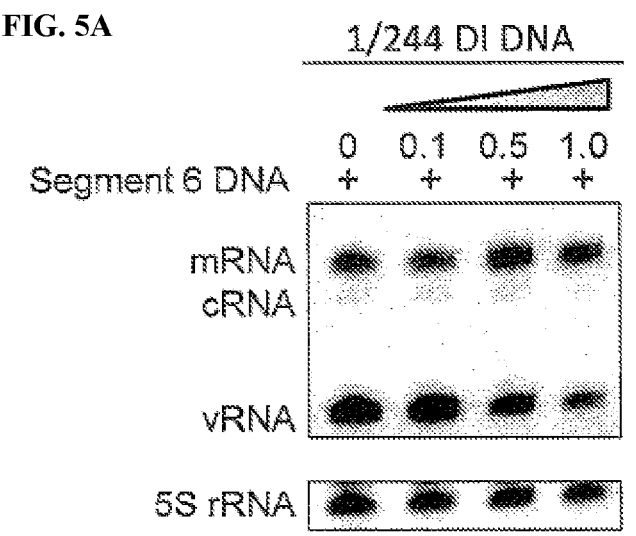
FIG. 5A shows northern blot analysis of levels of RNA transcribed from genome segment 6 in the absence or presence of increasing amount of 1/244 DI RNA. Quantitation of viral RNA levels from three independent experiments by phosphorimaging analysis is shown in FIG. 5B. The values of band intensities were normalized against the relevant 5S rRNA and are expressed as a percentage of the maximum value for each RNA analysed. Basal levels of vRNA generated from the target plasmid were subtracted from the total. The error bars represent the standard error of the mean from 3 independent experiments. vRNA(■), mRNA(▲) and cRNA(▼).
Figure 5B:
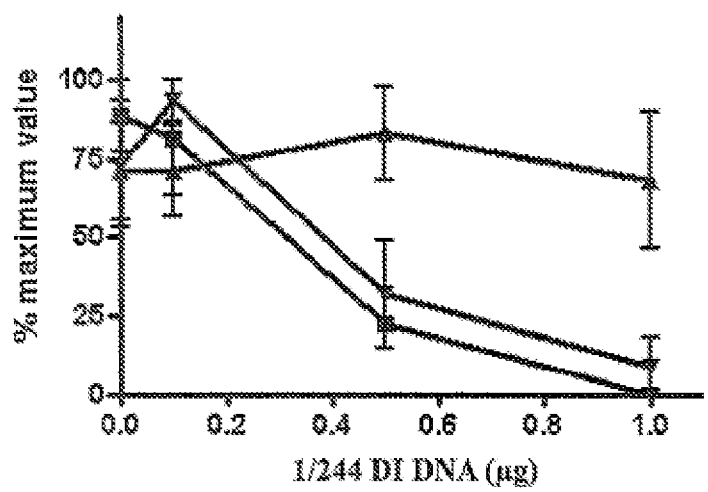
FIG. 5 shows RNA analysis of influenza segment 6-directed RNA synthesis by primer extension in the presence of influenza 1/244 DI RNA.

To determine how the target RNA affects the specificity of DI RNA-mediated inhibition of RNA synthesis and accumulation we used segment 6 as target. FIG. 5A shows that mRNA production by segment 6 was unaffected by 1/244 DI RNA even at the highest amount of 1/244 DI plasmid transfected (1 μs), while cRNA and vRNA levels were reduced. Quantitation of 3 separate assays showed that 0.5 μs 1/244 DI RNA decreased segment 6-encoded vRNA to 23% and cRNA to 32% of the control value (FIG. 5B).

The data described above demonstrate that the segment 1-derived 1/244 DI RNA differentially affected the levels of RNAs produced from genome segment 1 and segment.

Figure 6A:
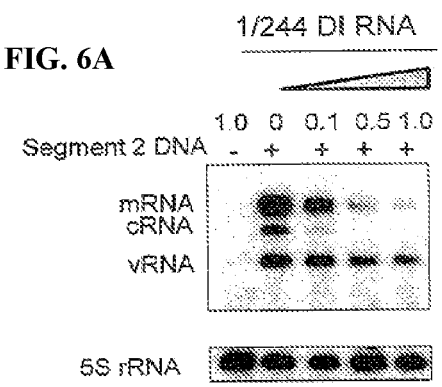
FIG. 6 shows RNA analysis of the effect of influenza 1/244 DI RNA on the level of RNA transcribed from influenza genome segments 2 and 3. Northern blot analysis of RNA derived from segment 2 (FIG. 6A) and segment 3 (FIG. 6C) in the presence of increasing amounts of 1/244 DI RNA was carried out as described for FIG. 4. Quantitation of viral RNA levels from two independent experiments is shown in FIG. 6B and FIG. 6D. The error bars represent the range of data for two experiments. vRNA(■), mRNA(▲) and cRNA(▼).
Figure 6C:
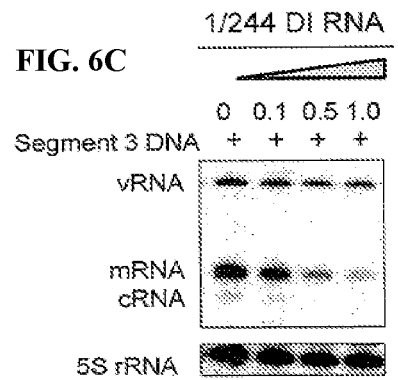
Figure 6B:
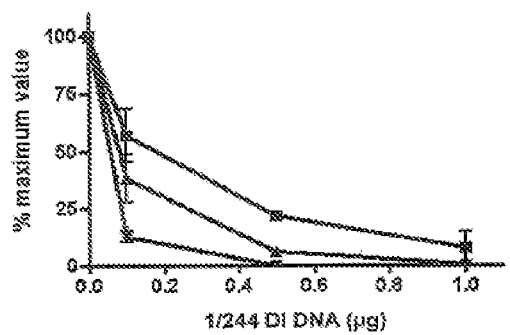
Figure 6D:
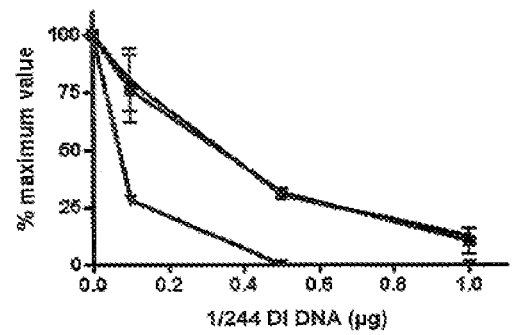
Figure 8:
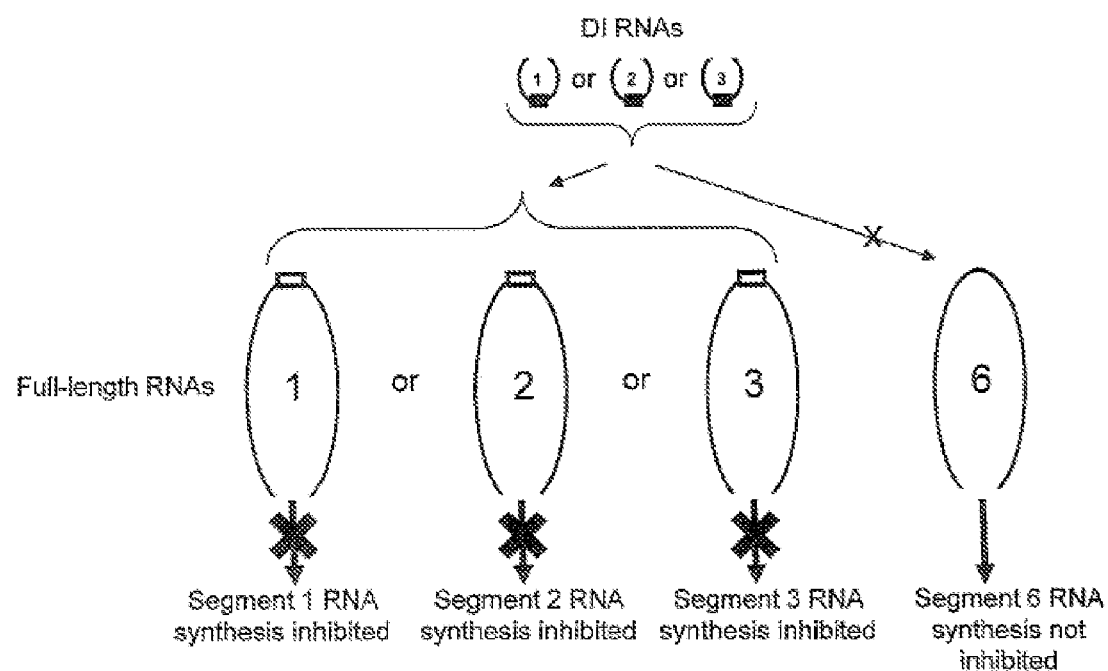
FIG. 8 shows a schematic diagram of the specific inhibition of RNA synthesis effected by full-length segments 1 or 2 or 3 by defective interfering influenza RNAs derived from segments 1 or 2 or 3. RNA synthesis carried out by full-length segment 4 (not shown) or 6 was not inhibited. The solid boxes on DI RNAs 1, 2 and 3 represent the common interacting element, and the open boxes on full-length segments 1, 2 and 3 represent its counterpart. The latter is absent from full-length RNA 6.

Since there was also cross-segment interference between the DI RNAs 2/265 or 3/262 and expression of GFP by segment 1-GFP (FIG. 3), we investigated the effects of 1/244 DI RNA on the RNA levels transcribed from segments 2 and 3. Cells were transfected with different amounts of 1/244 DI plasmid DNA, the helper plasmids encoding the virus polymerase and NP proteins and a plasmid directing the synthesis of either full-length segment 2 or segment 3 vRNAs. FIG. 6A and FIG. 6C show that 1/244 DI RNA reduced the levels of all three RNAs synthesized by segment 2 or 3. Inhibition of segment 2-derived RNAs more closely resembled that seen with the segment 1 target (FIG. 4A) than with the segment 6 target RNA (FIG. 5A). There was a greater reduction in segment 2 cRNA and mRNA levels than in its vRNA level. However, four-fold more 1/244 plasmid DNA was required to reduce the segment 2 mRNA level to 13% of the control than was needed with the segment 1 target RNA. There was a less pronounced reduction of mRNA, cRNA and vRNA levels with the segment 3 target. The data clearly show that 1/244 DI RNA reduces levels of mRNA synthesized from segments 1, 2 and 3.

1/244 DI RNA Inhibits Synthesis of its own Negative Sense vRNA but not its own Positive Sense RNA In light of the ability of 1/244 DI RNA to differentially reduce the level of segment 1-encoded RNAs, we investigated whether or not the levels of the positive and negative-sense RNAs synthesised from the 1/244 DI RNA in the same system were also affected. The gels used to analyse these RNAs could not separate the cRNA and mRNA which co-migrated. FIG. 7A and FIG. 7B show that in the presence of the segment 1-GFP target, 1/244 DI positive-sense RNA levels increased as amounts of transfected 1/244 DI plasmid were increased. Thus these were maximal in the samples in which the segment 1-GFP mRNA and cRNA levels were at a minimum (FIG. A, FIG. 4B). This shows clearly that 1/244 DI RNA does not inhibit all influenza polymerase-directed transcription. However, the level of 1/244 DI-specific vRNA was reproducibly maximal with 0.1 μg 1/244 plasmid DNA, and decreased to 13% of the maximum value with 0.5 μg plasmid and to 4% with 1 μg plasmid (FIG. 7B) demonstrating that a high concentration of 1/244 DI RNA reduces the level of its own de novo produced vRNA. When 1/244 plasmid DNA was titrated in cells in the absence of any target RNA the resulting levels of 1/244 positive-sense RNA and 5 vRNA were similar to those in the presence of segment 1 target RNA (FIG. 7C, FIG. 7D).

Discussion

Despite the many years spent investigating DI influenza viruses, understanding of the mechanism of action of interference in vitro, and protection from disease in vivo remains elusive. A commonly held hypothesis is that the small size of the DI RNA allows it to outcompete the full-length genome due to a faster replication rate, and that the proportion of virus particles containing DI genomes simply reflects the relative levels of DI and intact genomes present within infected cells (Roux et al. 1991; Marriott and Dimmock 2010). A second hypothesis is that DI RNA has an advantage in competing for a limiting viral or host factor. However, there is little experimental evidence to support either of these hypotheses with DI genomes in general, and none for influenza DI virus. More recently, a third hypothesis suggested that the influenza virus DI RNA interferes at the level of packaging of genomic RNAs into virions (Duhaut and McCauley 1996). Further, underlying this was the suspicion that different influenza DI sequences have different biological properties (Duhaut 1998; Dimmock et al. 2008). Understanding the interference process has the potential to provide new approaches for the development of novel antivirals based on DI genomes and the discussion below indicates how the data presented in this report have advanced our understanding of DI influenza viruses.

1/244 DI RNA Interferes with Packaging of the Cognate Segment 1 Virion RNA

FIG. 2 shows that 1/244 DI RNA interferes specifically with packaging of its cognate full-length segment 1 RNA into nascent virions. Thus, 1/244 DI RNA acts in a segment-specific manner similar to that reported for the segment 1-derived 317 DI RNA in a non-cloned virus population enriched by limit dilution passage (Duhaut and McCauley 1996), or for cloned 317 DI virus (Duhaut and Dimmock 2002). This is consistent with current models suggesting that packaging of influenza virus genome segments requires the formation of arrays or complexes consisting of a single copy of each genome segment and that these arrays act as a single structure which becomes packaged into new virus particles (Harris et al. 2006; Noda et al. 2006). Our data indicate that competition for packaging with the cognate full-length genomic RNA is likely to be a common feature of all influenza virus DI RNAs, and demonstrates that preferential packaging of DI RNA enriches the population of DI virus particles at the expense of infectious virus.

1/244 DI RNA Interferes with Expression of the Cognate Segment 1, with Segments 2 and 3 Virion RNAs Analysis of the effect of the DI genome on mRNA synthesis from a segment 1 target genome RNA in the absence of virus particle synthesis, measured directly or by monitoring expression of a reporter gene showed that 1/244 DI RNA interfered with the RNA synthesis directed by a segment 1-derived target (FIG. 3). The considerably weaker level of inhibition mediated by full-length segment 4 (FIG. 3E) or segment 6 vRNAs (FIG. 3F and FIG. 3G) confirmed that this effect is specific to DI RNA. The inhibition seen with increasing levels of plasmid DNA expressing genome segments 4 and 6 may be due to high levels of these RNAs competing for a limiting factor such as the virus polymerase complex in the transfected cells. Thus influenza DI RNAs can interfere by mechanism(s) other than, and in addition to, segment-specific packaging.

DI RNA can Differentially Affect the Steady State Levels of the Different RNAs Expressed by the Target RNA The synthesis of positive (mRNA and cRNA) and negative-sense (vRNA) virus RNA are distinct processes as evidenced by the effect of specific mutants abolishing the function of one or the other (Jorba et al. 2009; Yuan et al. 2009), and the data presented here show that 1/244 DI RNA differentially affects the steady state levels of the different RNA products expressed by its target. Increasing amounts of transfected 1/244 DI RNA led to a dramatic reduction in full-length segment 1-derived mRNA and cRNA levels with a lesser effect on vRNA levels; four-fold more plasmid DNA was required to reduce vRNA to the same levels as mRNA and cRNA (FIG. 4A, FIG. 4B). Thus, the segment 1-derived 1/244 DI RNA specifically and preferentially reduced the level of positive-sense RNA made from a cognate target, with considerably less effect on negative-sense vRNA. This differs from an earlier report that the segment 1-derived 317 DI virus did not inhibit RNA synthesis, although this study did not use molecularly cloned DI virus (Duhaut and McCauley 1996). Surprisingly, 1/244 DI RNA also strongly inhibited mRNA synthesis from segments 2 and 3 (FIG. 6) suggesting that genome segments 1-3 (encoding components of the virus RNA polymerase) share common feature(s) that permit the inhibitory action of segment 1 DI RNAs. This appeared to be reciprocal as DI RNAs 2/265 and 3/262 also inhibited GFP expression from the segment 1 target (FIG. 3). This is the first demonstration that an influenza DI RNA can dramatically affect gene expression from a genome segment other than that from which it arose. At levels of 1/244 DI RNA which strongly reduced the level of target mRNA from segment 1, its own positive-sense RNA levels were maximal (FIG. 7A, FIG. 7B). Thus, in a dose-dependent manner 1/244 DI RNA preferentially allows transcription from itself while suppressing synthesis from the target segment 1 RNA.

Data in FIG. 4 and FIG. 7 provide the first evidence for enrichment of DI RNA. As the amount of transfected 1/244 DNA was increased there was a proportionate decrease in all three RNAs synthesised by the segment 1 target RNA (FIG. 4), whereas with transfection of 0.1 µg 1/244 DNA all RNAs transcribed from the 1/244 DI RNA template increased (FIG. 7). However, the situation is complicated as higher levels of plasmid cause a reduction in the amount of DI vRNA. This reduction appears to be a feature of factors that we do not yet understand. The observed decline in DI vRNA levels with increasing input of DI plasmid suggests there could be an imbalance in the synthesis of the three DI RNAs in which vRNA, which is templated by, and therefore dependent on, DI cRNA, loses out. This appears to be a self-limiting phenomenon which has not previously been described for DI virus systems. Overall these data show an inverse relationship in the levels of full-length and DI RNAs and begin to provide an explanation for the process by which DI virus becomes dominant over infectious virus.

The reduction of mRNA levels by 1/244 DI RNA was not observed when segments 4 or 6 were used as the target, indicating that 1/244 DI RNA does not interfere with all genome segments and acts selectively on the synthesis of positive-sense RNA from segments 1, 2 and 3 (FIG. 3 and FIG. 5A). Segments 1, 2 and 3 direct the synthesis of considerably lower levels of mRNA relative to vRNA compared with other genome segments. Additionally, it has been suggested that segments 1-3 mRNAs are produced by primary transcription rather than from newly synthesised vRNA (Smith and Hay 1982; Hatada et al. 1989). Thus transcription from the three largest genome segments appears to differ from transcription from the other segments, and the data presented here suggest that DI RNAs derived from segments 1, 2 or 3 may suppress transcription from all three segments by affecting this different transcription process. Large quantities of short RNA molecules referred to as svRNA or leRNA are produced during influenza infection (Perez et al. 2010; Umbach et al. 2010), and these may play a role in the switch from transcription to replication (Perez et al. 2010). If correct, this raises the possibility that a DI RNA may serve as the template for the production of svRNAs, which in turn modulate the production of the replication products vRNA, cRNA, and mRNA. The mechanism(s) by which these different synthetic processes in segments 1, 2 and 3 are affected is not known, and it will be of interest to investigate if the ability to regulate replication products is common to all DI RNAs or if it is a property only of specific DI RNAs. This may mean that the huge number of DI RNAs that can be produced during an influenza virus infection, vary in their efficiency of interference. Further exploration will provide insights into the differential regulation of transcription of influenza genome segments.

A model for Interference by 1/244 DI RNA

DI mRNAs that retain the AUG initiation codon of the major open reading frame have the potential to be translated into truncated PB2 peptides, as demonstrated for some segment 1-derived DI RNAs (Akkina et al. 1984), and similar short polypeptides containing the PA protein binding domain of the PB1 strongly inhibited the virus RNA polymerase activity (Wunderlich et al. 2009; Manz et al. 2011). Thus in principle, a truncated PB2-related polypeptide derived from 1/244 DI RNA could also exert a dominant negative effect on the virus polymerase activity. However, we excluded this possibility by generating a form of 1/244 DI RNA in which the AUG initiation codon for PB2 and two further downstream in-frame AUG codons that could direct synthesis of a short polypeptide from the PB2 ORF were mutated (Meng et al., submitted for publication). We confirmed that this 1/244 AUG knock-out DI RNA was indistinguishable in action from that of the parental 1/244 DI RNA. It generated vRNA and mRNA to similar levels as 1/244 DI RNA, and inhibited GFP expression from segment 1 as seen with 1/244 DI RNA. Further, DI virus containing the 1/244 AUG knockout RNA protected mice from disease following challenge with influenza virus in a similar manner to 1/244 DI virus. These data show that the activity of 1/244 DI is solely an RNA-based phenomenon.

The ability of influenza virus DI RNAs to supplant their cognate genome segment during the packaging process explains their amplification in virus preparations. However, the data above exclude the widely held view that the interference mechanism within cells results solely from the ability of the DI RNA to be replicated faster than the longer, cognate full-length RNA. Rather the DI RNAs also specifically target virus RNA synthesis. The data shown here indicate that the primary consequence of 1/244 DI RNA-mediated interference within the cell is the targeted inhibition of RNA synthesis directed by full-length RNA segments 1, 2 and 3, and that DI RNAs derived from segments 2 and 3 also inhibit RNA synthesis from full-length segment 1.

Example 2—Protein Expression Encoded by DI RNA is not Required for Interference

Material and Methods

Plasmids and Production of Infectious Virus by Reverse Genetics

Plasmids encoding the 8 gene segments of the A/WSN strain of A/WS/33 and plasmids expressing the polymerase and NP proteins (Neumann et al. 1999), and the vector expressing 244 DI RNA from PolI promoters have been previously described (Dimmock et al. 2008; Duhaut and Dimmock 2002). 244 RNA is 395 nucleotides and was derived from segment 1 of A/Puerto Rico/8/34 (H1N1). The segment 1 target, segment 1-GFP, was created by amplifying the GFP ORF by PCR and inserting this into pPolI-220 (Duhaut and Dimmock, 2000) such that the GFP ORF was in frame with the PB2 ORF, giving plasmid seg 1-GFP which expresses segment 1-GFP RNA (Meng et al. 2012). The GFP reporter plasmid retains the exact 5' (220 nt) and 3' (48 nt) terminus of segment 1. Human 293T cells were transfected with plasmids as previously described (Dimmock et al. 2008). Briefly, 70% confluent 293T cells in a 12-well plate were transfected using TransITLT1 transfection reagent (Mirus) with 8 PolI expression plasmids encoding viral sense RNA and cDNA plasmids for expression of PB2, PB1, PA and NP proteins, with or without pPolI-244 or pPolI-244 knock-out. The transfected cells were then incubated at 37° C. overnight before co-culture with MDCK cells in a 25 cm² flask. Finally virus in tissue culture fluids was passaged once in embryonated chicken's eggs and allantoic fluids harvested to produce a stock of virus (Dimmock et al. 2008).

The virus produced in embryonated chicken's eggs is a mixture of 244 DI virus or 244 AUG knock-out DI virus packaged in A/WSN virion proteins and infectious helper A/WSN virus. These were purified by differential centrifugation through sucrose, and resuspended in PBS. Stocks were standardized according to their haemagglutination titre and stored in liquid nitrogen. The DI virus stock was UV-irradiated to remove helper virus infectivity using a short burst (40 seconds) of UV irradiation at 253.7 nm (0.64 mW/cm$^2$). This is 'active DI virus'. The UV target is viral RNA, but UV has relatively little effect on the DI RNA because of its small target size, 395 nt compared with 13,600 nt for infectious virus. Longer UV irradiation (8 minutes) inactivates protecting activity for mice, but does not affect haemagglutinin or neuraminidase activities, and so controls for any immune system-stimulating or receptor-blocking effects of 244 DI virus particles ('inactivated DI virus'). The yield of 244 AUG knock-out DI A/WSN virus and its behaviour on purification were very similar to 244 DI A/WSN virus (data not shown).

Mutation

Two sequential steps of site-directed mutagenesis were carried out to mutate the three start codons in the 244 DI RNA. A pair of primers were used for site-directed mutagenesis to convert the first AUG to AUC using a pPolI-244 plasmid as template and pfu DNA polymerase (Promega). The mutation was confirmed by sequencing. The second round of site-directed mutagenesis was done using primers which altered the second and third start codons of AUG to AUC using the construct produced from the first round of mutagenesis. The resulting construct was again confirmed by sequencing.

Northern Blot Analysis

Total cellular RNA was isolated from DI infected cells using Trizol. Poly A containing mRNA was selected using a GenElute Direct mRNA preparation kit (Sigma) according to the manufacturer's instructions. Non-polyadenylated RNA that did not bind to the column during mRNA preparation was retained. Aliquots of total RNA, mRNA and non-polyadenylated RNA were separated by glyoxal-agarose gel electrophoresis. After electrophoresis, the RNA was transferred onto Hybond-N membrane (GE Healthcare) overnight using 20×SSC. The membrane was then baked at 80° C. for 2 h. A full length negative sense segment 1 probe was prepared by in vitro transcription in the presence of DIG-UTP (Roche) from a PCR product containing a bacteriophage T7 promoter. The membrane was hybridized with the DIG-labelled probe overnight and the signal was detected using a digoxigenin-specific AP FAb antibody fragment and CSPD substrate (Roche).

Primer Extension Analysis

Primer extension analysis was carried out on total cellular RNA (Rehwinkel et al. 2010). Total RNA (2 μg) was mixed with [$^{32}$P]5'-end labelled primers and dNTP in a total volume of 13 μl. The mixture was heated at 65° C. for 5 min and placed on ice for 1 min. 2× first Strand Buffer, 20 mM DTT, and 100 U SuperScript III reverse transcriptase (Invitrogen) were added and further incubated at 55° C. for 1 h. The reaction was terminated by heating at 95° C. for 5 min with gel loading dye II (Ambion). The transcription products were resolved on a 6% (w/v) polyacrylamide gel containing 7 M urea in TBE buffer and detected by phosphor imaging.

Interference Measured by the Inhibition of GFP 293T cells were transfected with the segment 1-GFP RNA expressing plasmid, plasmids expressing PB1, PB2, PA and NP proteins, and increasing amounts of an additional PolI plasmid expressing a 244 DI or 244 AUG knock-out DI RNA, At 2 days post-transfection, the cultures were examined for GFP expression. Digital images of the cell monolayers were taken by phase-contrast and epifluorescence microscopy. Five field fluorescence images were randomly selected and analysed for the proportion of the visualised area expressing GFP using the HCimage software (Hamamatsu). The visualisation detects cells expressing a range of GFP levels to include those that may have been transfected with different levels of the reporter plasmids. A mean was calculated to give the percentage of the GFP positive area per monolayer.

Protection of Mice from Influenza with DI Virus

In order to assess the degree of protection afforded by DI virus, C3H/He-mg mice were inoculated intranasally under light ether anaesthesia with A/WSN alone (10 LD$_{50}$ or 1000 ffu), a mixture of A/WSN+active DI virus, or A/WSN+ inactivated DI virus. Mice were subsequently monitored for clinical disease according to our standard protocol and for weight loss as previously described (Dimmock et al. 2008). Surviving mice were challenged 3 weeks after infection with a high dose of A/WSN (10,000 LD$_{50}$) to determine their immune status.

Results

Coding Potential of 244 DI RNA

244 DI RNA, a molecule of 395 nucleotides, arose from segment 1 of PR8 as a result of one or more deletion events that left 244 nucleotides at the 3' end and 151 nucleotides at the 5' end of the positive sense RNA (Dimmock et al. 2008). 244 RNA retains the signals at the terminus of the genome segment that direct transcription of mRNA (FIG. 1). During replication influenza virus makes two forms of positive sense RNA. Replication involves synthesis of positive-sense (cRNA) copies of the genome vRNAs of the infecting virus, which in turn are used as templates for synthesis of new vRNAs (Palese and Shaw, 2007). Influenza virus mRNA synthesis is initiated using a primer cleaved from the capped 5' end of host mRNA and its synthesis terminates before the end of the template vRNA, prior to polyadenylation (Dias et al. 2009; Fechter et al. 2003; Guilligay et al. 2008; Plotch et al. 1981). Thus the mRNA differs from the positive sense replication intermediate cRNA in having the primer-derived 5'-extension, and in being truncated and polyadenylated at the 3' end. To confirm that 244 DI RNA can direct the synthesis of mRNA the RNAs present in cells infected with 244 DI virus were investigated. Northern blot analysis using a segment 1 specific probe to detect positive sense RNA identified two polyadenylated virus mRNAs in infected cells (FIG. 2A). The larger mRNA of approximately 2.3 kb is consistent with mRNA derived from the full length genome segment 1 provided by the helper virus. The smaller mRNA of approximately 500 bases indicates that the 244 DI RNA directs the synthesis of mRNA. The positive sense RNA seen in the non-polyadenylated RNA fraction is cRNA and as expected this can be seen to be slightly smaller than the 244 DI-derived mRNA.

Figures 9A, 9B:
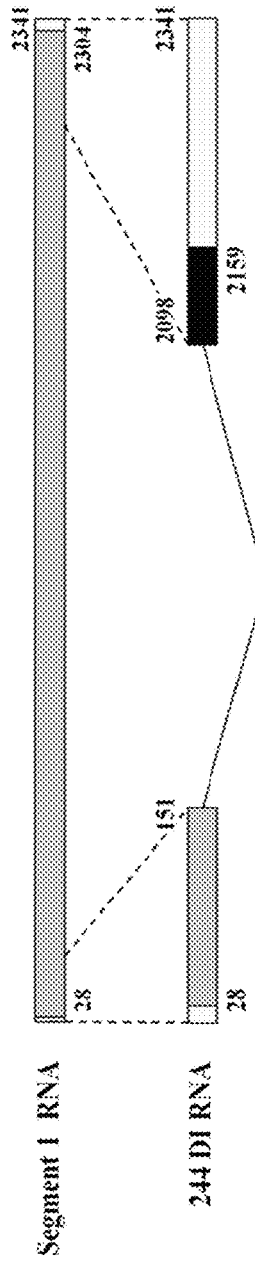
FIG. 9A is a schematic diagram showing the relationship of influenza genome segment 1 RNA and the segment 1 244 DI RNA. Numbers indicate nucleotide positions based on the sequence of positive sense influenza PR8 genome segment 1. The nucleotide positions of the breakpoints in the DI RNA genome are shown. Numbers below the RNAs indicate the nucleotide positions of the first nucleotide of the initiation and termination codons for the amino acids encoded by the mRNA transcribed from the full length segment 1 and 244 DI RNAs. The gray shading indicates PB2 coding sequence and the black shading indicates a new reading frame accessed following the breakpoint in 244 DI RNA.
FIG. 9B shows the sequence of 244 DI RNA in cRNA sense indicating the open reading frame, and the predicted protein sequence in single letter amino acid code. The 35 residue PB1 binding domain of PB2 is indicated by the dark grey box, and the 22 residue mitochondrial interaction domain of PB2 is indicated by the light grey box. The boxed amino acid sequence appeared de novo downstream from the central deletion that gave rise to 244 DI RNA This sequence did not arise from the PB2 ORF. The three G→C mutations at nucleotide positions 30, 60 and 111 used to mutate the in-frame AUG initiation codons are shown in bold and underlined.

The mRNA transcribed by 244 DI RNA contains the translation start codon of the PB2 open reading frame 1 (ORF-1) giving the 244 DI RNA capacity to encode a protein comprising the first 41 amino acid residues of PB2 fused to 21 amino acid residues translated from a different reading frame generated as a result of the deletion, making a protein of 62 residues in total (FIG. 9B). This putative protein contains the entire PB I-binding domain of residues 1-35 (Sugiyama et al. 2009) and the mitochondrial localisation domain of residues 1-22 (Carr et al. 2006). The PB2 ORF has three possible AUG start codons. The sequence context for the first AUG (the authentic start codon for PB2)

is very good, while the second and third are poor. However, to be sure there could be no translation initiation we mutated all three possible start codons (to AUC); the sequence was then confirmed. The new RNA is known as 244 AUG knock-out DIRNA.

244 AUG Knock-Out DIRNA and 244 DI RNA Interfere with the Expression of a Segment 1 RNA in Cell Culture to a Similar Extent RNAs were harvested 2 days after 293 T cells were transfected with plasmid encoding either the 244 DI RNA or the 244 AUG knock-out DI RNA together with plasmids expressing the PB2, PB1, PA and NP proteins. Primer extension analysis showed that similar amounts of mRNA and vRNA were synthesized by the 244 and 244 AUG knock-out DI RNAs confirming that transcription was unaffected by the mutations in the 244 AUG knock-out DI RNA (FIG. 10B).

To investigate the interfering ability of 244 AUG knock-out RNA, we used a GFP expression assay in which transcription and replication of a segment 1 RNA in which most of the PB2 coding region had been replaced with GFP (segment 1-GFP) were enabled by co-transfection of plasmids expressing PB1, PB2, PA and NP proteins into 293T cells.

Figure 11A:
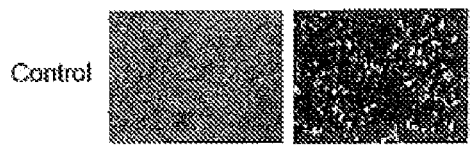
FIG. 11 shows fluorescence assay analysis for the interfering activity of 244 AUG knock-out DI RNA and 244 DI RNA based on the inhibition of expression of fluorescence by an influenza segment 1 RNA expressing GFP. 293T cells were transfected with plasmids expressing the segment 1-GFP RNA, plasmids expressing PB1, PB2, PA and NP proteins, and increasing amounts of plasmids expressing 244 AUG knock-out DI RNA (FIG. 11C) or 244 DI RNA (FIG. 11B). Cells were examined for fluorescence at 2 days post transfection. Cell monolayer images were recorded by phase-contrast microscopy (left of each column) and epifluorescence microscopy (right). The amount of plasmid expressing the DI RNA is shown on the left. Control cells (FIG. 11A) were transfected with an empty DI vector (1 µg).
FIG. 11D shows quantitation of fluorescence generated in cells in the presence of transfected plasmids expressing the 244 AUG knock-out DI RNA (grey) and the parental wild type (wt) 244 DI RNA (white). The range of two independent experiments is shown.
Figure 11A:
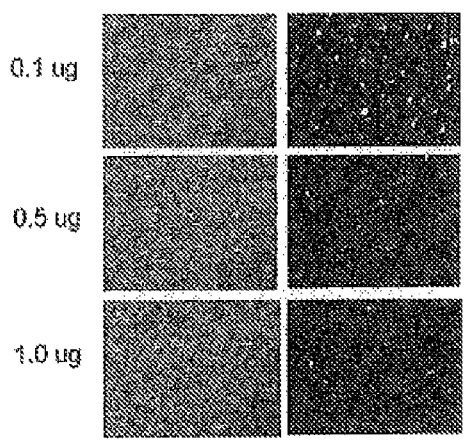
Figure 11A:
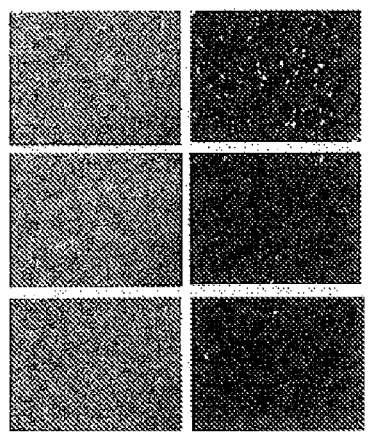
Figure 11D:
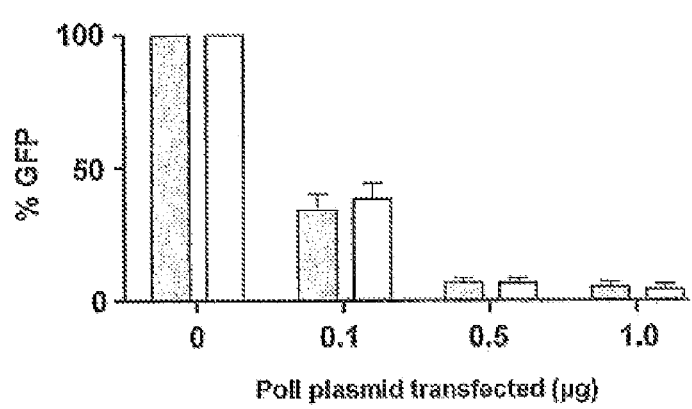

This system permits viral RNA synthesis but not virus particle formation as plasmids encoding key structural proteins (HA, NA, M1 and M2) were not included. The effects of co-transfected DI RNA-encoding plasmids were assessed by monitoring GFP fluorescence. FIG. 11 compares the expression of fluorescence in a positive control culture in the absence of either DI RNA with cultures transfected with various amounts of 244 plasmid or 244 AUG knock-out plasmid. This showed that both plasmids strongly inhibited fluorescence in a dose-dependent manner, for example 0.5 µg of 244 plasmid or 244 AUG knock-out plasmid both inhibited GFP fluorescence by over 90% (FIG. 11D).

Figure 12A:
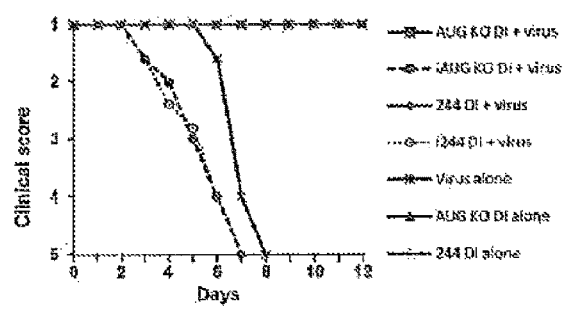
FIG. 12A and FIG. 12C, mean clinical score.
Figure 12B:
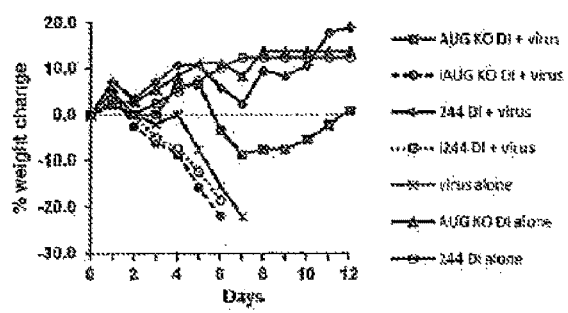
FIG. 12B and FIG. 12D, mean weight change.

244 AUG Knock-Out DI Virus Protects Mice from a Lethal Influenza A Virus Challenge We compared the protection activity of 244 DI and 244 AUG knock-out DI RNA in our C3H/He-mg mouse model using A/WSN as the challenge virus (Dimmock et al. 2008). Mice were infected intranasally under light anaesthesia with A/WSN alone, or with A/WSN+244 DI virus, or A/WSN+244 AUG knock-out DI virus. Other infected groups received DI virus which had been UV-irradiated for 8 minutes to destroy DI protecting activity and to control for any non-specific effects of the DI virus inoculum. Mice were monitored for clinical disease and weight loss. FIG. 12A, and FIG. 12B show that the virus-infected control mice all became seriously ill with substantial weight loss, and had to be culled. In contrast none of the mice treated with 244 DI virus or 244 AUG knock-out DI virus developed any sign of clinical disease. Mice treated with 244 DI virus and 244 AUG knock-out DI virus both showed a transient drop in weight (FIG. 12B). Weight loss is the more sensitive criterion of disease and it is not uncommon to see this range of variation in the absence of any clinical disease. As expected from earlier data (Dimmock et al. 2008), mice treated with UV-inactivated DI virus were not protected. We have shown previously that animals treated with 244 DI virus simultaneously with infectious virus generate protective immunity that prevents disease following subsequent challenge with a high dose of the same virus in the absence of further treatment with DI virus (Dimmock et al. 2008).

Figure 12C:
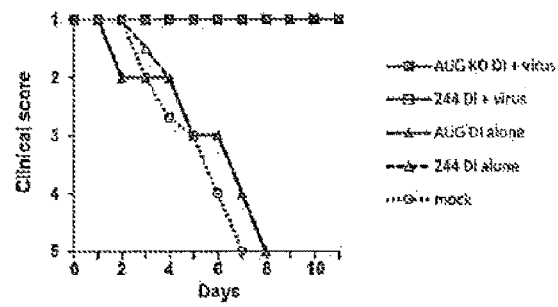
Figure 12D:
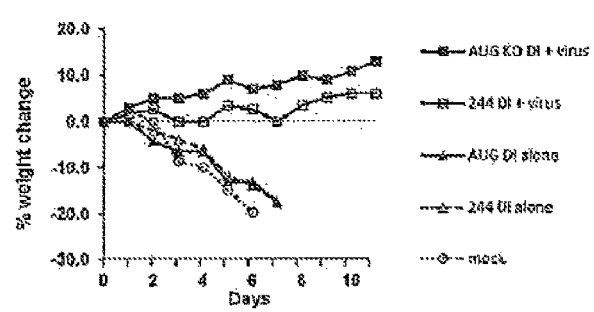

Animals treated with the 244 knock-out DI virus were solidly immune to further challenge with a high dose of A/WSN showing that they had been infected even though they developed no sign of clinical disease (FIG. 12C, FIG. 12D).

Discussion

Although DI influenza viruses have been known for over 60 years, there has been little indication of the molecular mechanisms by which their in vitro interfering activity or in vivo protecting activity operate. Initially the problem was insoluble as natural DI virus preparations contain a diversity of defective RNA sequences and thus the biological properties of individual DI sequences could not be analysed. However, the use of cloned DI viruses generated using reverse genetics has allowed us to address this problem. Our recent work has shown that 244 DI RNA which is derived from genome segment 1 interferes in three ways: competition with the cognate full-length segment for packaging, interference with the synthesis and/or accumulation of the polymerase encoding full-length virion RNA segments 1, 2 and 3, and stimulation of type I interferon in vivo. Here, we have shown that influenza 244 DI RNA directs the synthesis of polyadenylated mRNA (FIG. 10). The mRNA is larger than the positive sense cRNA as expected for all influenza virus mRNAs indicating that the DI RNA is a template for transcription. The mRNA produced from 244 DI RNA will therefore contain a 5' cap and poly A tail and potentially be available for translation into protein. The sequence of the 244 DI RNA predicts that DI mRNA can be translated into a protein that shares the amino terminal 41 amino acid residues of PB2. This region of PB2 has been shown to bind to the PB1 protein of the polymerase complex and also be localised in the host cell mitochondria (Carr et al. 2006; Sugiyama et al. 2009).

A mutant 244 DI RNA in which all three in-frame AUG translation initiation codons from the PB2 ORF were converted to AUC, and which was therefore unable to express the PB2-related protein, retained the properties of the original 244 DI RNA. The 244 AUG knockout DI RNA was able to interfere with gene expression from influenza virus segment 1 in vitro to the same extent as seen with 244 DI RNA (FIG. 10B and FIG. 11). Most importantly 244 AUG knock-out DI RNA retained the ability to protect mice from a disease following administration of a lethal dose of influenza virus (FIG. 12). Thus the mutation had no effect on interference in vitro and protection in vivo by 244 DI RNA.

We conclude that in vitro interference and in vivo protection against influenza virus disease are not mediated by the truncated PB2 peptide that is encoded, and may be synthesized by 244 DI RNA, and that these processes are therefore controlled by the DI RNA molecule itself.

The invention claimed is:

1. A method to identify an antiviral agent, comprising:
   in a host cell, exposing an influenza A virus to a test defective interfering (DI) influenza A virus RNA having a deletion in one of RNA segments 1, 2, or 3;
   monitoring for the production of RNA from each of segments 1, 2, and 3 of the influenza A virus in the presence of the test DI influenza A virus RNA; and
   identifying the antiviral agent as being a test DI virus RNA that interferes with production of RNA from each of segments 1, 2, and 3 of the influenza A virus.

2. The method according to claim 1, wherein the RNA production from each of segments 1, 2 and 3 of the influenza A virus is monitored in a separate assay.

3. The method according to claim 1, wherein the RNA production from each of segments 1, 2, or 3 of the influenza A virus comprises cRNA, mRNA and/or vRNA.

4. The method according to claim 3, wherein both cRNA and mRNA production are monitored.

5. The method according to claim 1, wherein one or more of segments 1, 2 or 3 of the influenza A virus is provided as a construct.

6. The method according to claim 5, wherein the host cell is transfected with one or more nucleic acids each comprising one or more of segments 1, 2, and 3 of the influenza A virus.

7. The method according to claim 5, wherein each of said segments 1, 2, and 3 of the influenza A virus is provided on a separate plasmid.

8. The method according to claim 5, wherein the construct comprises a reporter gene, such that a reduction in production of RNA from a segment reduces expression of the reporter gene.

* * * * *

SEQUENCE LISTING

<160> NUMBER OF SEQ ID NOS: 25

<210> SEQ ID NO 1
<211> LENGTH: 395
<212> TYPE: DNA

<213> ORGANISM: Influenza virus

<400> SEQUENCE: 1

| | | | | | |
|---|---|---|---|---|---|
| agcgaaagca | ggtcaaatat | attcaatatg | gaaagaataa | agaactaag | aaatctaatg | 60 |

-continued

| | |
|---|---:|
| tcatcgtcaa tgatgtggga gattaatggt cctgaatcag tgttggtcaa tacctatcaa | 1680 |
| tggatcatca gaaactggga aactgttaaa attcagtggt cccagaaccc tacaatgcta | 1740 |
| tacaataaaa tggaatttga accatttcag tctttagtac ctaaggccat tagaggccaa | 1800 |
| tacagtgggt ttgtgagaac tctgttccaa caaatgaggg atgtgcttgg gacatttgat | 1860 |
| accgcacaga taataaaact tcttcccttc gcagccgctc caccaaagca agtagaatg | 1920 |
| cagttctcct catttactgt gaatgtgagg ggatcaggaa tgagaatact tgtaaggggc | 1980 |
| aattctcctg tattcaacta caacaaggcc acgaagagac tcacagttct cggaaaggat | 2040 |
| gctggcactt taaccgaaga cccagatgaa ggcacagctg gagtggagtc cgctgttctg | 2100 |
| aggggattcc tcattctggg caaagaagac aggagatatg gccagcatt aagcatcaat | 2160 |
| gaactgagca accttgcgaa aggagagaag gctaatgtgc taattgggca aggagacgtg | 2220 |
| gtgttggtaa tgaaacgaaa acgggactct agcatactta ctgacagcca gacagcgacc | 2280 |
| aaaagaattc ggatggccat caattagtgt cgaatagttt aaaaacgacc ttgtttctac | 2340 |
| t | 2341 |

<210> SEQ ID NO 3
<211> LENGTH: 2341
<212> TYPE: DNA
<213> ORGANISM: Influenza virus

<400> SEQUENCE: 3

| | |
|---|---:|
| agcaaaagca ggtcaattat attcagtatg gaaagaataa agaactacg gaatctgatg | 60 |
| tcgcagtctc gcactcgcga gatactgaca aaaaccacag tggaccatat ggccataatt | 120 |
| aaaaagtaca catcggggag acaggaaaag aacccgtcac ttaggatgaa atggatgatg | 180 |
| gcaatgaaat acccaatcac tgctgacaaa aggataacag aaatggttcc ggagagaaat | 240 |
| gaacaaggac aaactctatg gagtaaaatg agtgatgctg gatcagatcg agtgatggta | 300 |
| tcaccttgg ctgtaacatg gtggaataga atggacccg tgacaagtac ggtccattac | 360 |
| ccaaaagtat acaagactta ttttgacaaa gtcgaaaggt taaacatgg aacctttggc | 420 |
| cctgttcatt ttagaaatca agtcaagata cgcagaagag tagacataaa ccctggtcat | 480 |
| gcagacctca gtgccaaaga ggcacaagat gtaattatgg aagttgtttt tcccaatgaa | 540 |
| gtgggagcca ggatactaac atcagaatcg caattaacaa taactaaaga gaaaaagaa | 600 |
| gaactccgag attgcaaaat ttctccctg atggttgcat acatgttaga gagaactt | 660 |
| gtacggaaaa caagatttct cccagttgct ggcggaacaa gcagtatata cattgaagtt | 720 |
| ttacatttga ctcaaggaac gtgttgggaa caaatgtaca ctccaggtgg agaagtgagg | 780 |
| aatgacgata ttgaccaaag cctaattatt gcggccagga acatagtaag aagagccgca | 840 |
| gtatcagcag atccactagc atctttattg gagatgtgcc acagcacaca aattggcggg | 900 |
| acaaggatgg tggacattct tagacagaac ccaactgaag aacaagctgt ggatatatgc | 960 |
| aaggctgcaa tggattgag aatcagctca tccttcagct ttggtgggtt tacatttaaa | 1020 |
| agaacaagcg gtcatcagt caaaaaagag gaagaagtgc ttacaggcaa tctccaaaca | 1080 |
| ttgaagataa gagtacatga ggggtatgag gagttcacaa tggtggggaa aagagcaaca | 1140 |
| gctatactaa gaaaagcaac cagaagattg gttcagctca tagtgagtgg aagagacgaa | 1200 |
| cagtcaatag ccgaagcaat aatcgtggcc atgtgttttt cacaagagga ttgcatgata | 1260 |
| aaagcagtta gaggtgacct gaatttcgtc aacagagcaa atcagcggtt gaaccccatg | 1320 |

| | |
|---|---:|
| catcagcttt taaggcattt tcagaaagat gcgaaagtgc tttttcaaaa ttggggaatt | 1380 |
| gaacacatcg acagtgtgat gggaatgatt ggagtattac agatatgac tccaagcaca | 1440 |
| gagatgtcaa tgagaggaat aagagtcagc aaaatgggtg tggatgaata ctccagtaca | 1500 |
| gagagggtgg tggttagcat tgatcggttt ttgagagttc gagaccaacg tgggaatgta | 1560 |
| ttattatctc ctgaggaggt cagtgaaaca cagggaactg agagactgac aataacttat | 1620 |
| tcatcgtcga tgatgtggga gattaacggt cctgagtcgg ttttggtcaa tacctatcaa | 1680 |
| tggatcatca gaaattggga agctgtcaaa attcaatggt ctcagaatcc tgcaatgttg | 1740 |
| tacaacaaaa tggaatttga accatttcaa tctttagtcc ccaaggccat tagaagccaa | 1800 |
| tacagtgggt tgtcagaac tctattccaa caaatgagag acgtacttgg acatttgac | 1860 |
| accacccaga taataaagct tctccctttt gcagccgctc caccaaagca aagcagaatg | 1920 |
| cagttctctt cactgactgt aaatgtgagg ggatcaggga tgagaatact tgtaaggggc | 1980 |
| aattctcctg tattcaacta caacaagacc actaaaagac taacaattct cggaaaagat | 2040 |
| gccggcactt taattgaaga cccagatgaa agcacatccg agtggagtc cgccgtcttg | 2100 |
| agagggtttc tcattatagg taaggaagac agaagatacg gaccagcatt aagcatcaat | 2160 |
| gaactgagta accttgcaaa aggggaaaag gctaatgtgc taatcgggca aggagacgtg | 2220 |
| gtgttggtaa tgaaacgaaa acgggactct agcatactta ctgacagcca gacagcgacc | 2280 |
| aaaagaattc ggatggccat caattaatgt tgaatagttt aaaaacgacc ttgtttctac | 2340 |
| t | 2341 |

<210> SEQ ID NO 4
<211> LENGTH: 2341
<212> TYPE: DNA
<213> ORGANISM: Influenza virus

<400> SEQUENCE: 4

| | |
|---|---:|
| agcaaaagca ggtcaattat attcagtatg gaaagaataa agaactacg gaacctgatg | 60 |
| tcgcagtctc gcactcgcga gatactaaca aaaaccacag tggaccatat ggccataatt | 120 |
| aagaagtaca catcagggag acaggaaaag aacccgtcac ttaggatgaa atggatgatg | 180 |
| gcaatgaaat atccaatcac tgctgacaaa aggataacag aaatggttcc ggagagaaat | 240 |
| gaacaaggac aaactctatg gagtaaaatg agtgatgctg ggtcagatcg agtgatggta | 300 |
| tcaccttgg ctgtgacatg gtggaataga aatggacctg tgacaaatac ggttcactat | 360 |
| ccaaaagtat acaagactta ttttgacaaa gtcgaaggt taaacatgg aacctttggc | 420 |
| cctgttcatt ttagaaatca agtcaagata cgccgaagag tggacataaa ccctggtcat | 480 |
| gcagacctca gtgccaagga ggcacaagat gtaattatgg aagttgtttt ccccaatgaa | 540 |
| gtgggagcca ggatactaac atcagaatca caattaacaa taaccaaaga gaaaaaagaa | 600 |
| gaactccgag attgcaaaat ttctcctttg atggttgcat acatgttaga gagggaactt | 660 |
| gtccgaaaaa cgagatttct cccagttgct ggcggaacaa gcagtatata cattgaagtt | 720 |
| ttacatttga ctcaaggaac gtgttgggaa caaatgtaca ctccaggtgg agaagtgagg | 780 |
| aatgacgatg ttgaccaaag cctaattatt gcagccagga acatagtgag aagagccgca | 840 |
| gtatcagcag atcactagc atctttattg agatgtgcc acagcacaca aattggcggg | 900 |
| acaaggatgg tggacattct taggcagaac ccgacggaag acaagctgt ggatatatgc | 960 |
| aaggctgcag tggattgag aatcagctca tccttcagct tggtggggtt acatttaaa | 1020 |
| agaacaagcg ggtcatcagt caaaagagag gaagaagtgc ttacaggcaa tctccaaaca | 1080 |

-continued

```
ttgaaaataa gagtacatga ggggtacgag gagttcacaa tggtggggaa aagagcaaca    1140
gctatactca gaaaagcaac caggagattg gttcaactca tagtgagtgg aagggacgaa    1200
cagtcaatag ccgaagcaat aatcgtggcc atggtgtttt cacaagagga ttgcatgata    1260
aaagcagtta gaggtgacct gaatttcgtt aacagggcaa atcagcggtt gaaccccatg    1320
catcagcttt taaggcattt tcagaaagat gcgaaggtgc ttttttcagaa ttggggaatt    1380 gaacacatcg acagtgtgat gggaatggtt ggagtattac cagatatgac tccaagcaca    1440
gagatgtcaa tgagaggaat aagagtcagc aaaatgggcg tggatgaata ctccagcaca    1500
gagagggtgg tggttagcat tgatcggttt ttgagagttc gagaccaacg tgggaatgta    1560
ttattatctc ctgaggaggt cagtgaaaca cagggaacag agagactgac aataacttac    1620
tcatcgtcaa tgatgtggga gattaacggt cctgagtcgg ttttggtcaa tacctatcaa    1680
tgggtcatca gaaattggga aactgtcaaa attcaatggt ctcagaatcc tgcaatgttg    1740
tacaacaaaa tggaatttga accatttcaa tctttagttc ctaaggccat tagaggccaa    1800
tacagtggat ttgtcagaac tctattccaa caaatgagag atgtacttgg gacatttgat    1860
accatccaga taataaagct tctcccttttt gcagccgctc caccaaagca aagcagaatg    1920
cagttctctt cattgactgt aaatgtgagg ggatcaggga tgagaatact tgtaaggggc    1980
aattctcctg tattcaacta caacaagacc actaaaagac taacaattct cggaaaagat    2040
gccggcactt taattgaaga cccagatgaa agcacatccg gagtggagtc cgctgtcttg    2100
agaggatttc tcattctagg taaggaagac agaagatacg gaccagcatt aagcatcaat    2160
gaactgagta accttgcaaa aggggaaaag gctaatgtgc taattgggca aggagacgtg    2220
gtgttggtaa tgaaacgaaa acgggactct agcatactta ctgacagcca gacagcgacc    2280
aaaagaattc ggatggccat caattaatgt tgaatagttt aaaaacgacc ttgtttctac    2340
t                                                                   2341
```

<210> SEQ ID NO 5
<211> LENGTH: 2341
<212> TYPE: DNA
<213> ORGANISM: Influenza virus

<400> SEQUENCE: 5

```
agcgaaagca ggcaaaccat ttgaatggat gtcaatccga ccttactttt cttaaaagtg     60
ccagcacaaa atgctataag cacaactttc ccttataccg gagaccctcc ttacagccat    120
gggacaggaa caggatacac catggatact gtcaacagga cacatcagta ctcagaaaag    180
gcaagatgga caacaaacac cgaaactgga gcaccgcaac tcaacccgat tgatgggcca    240
ctgccagaag acaatgaacc aagtggttat gcccaaacag attgtgtatt ggaagcaatg    300
gctttccttg aggaatccca tcctggtatt tttgaaaact cgtgtattga acgatggag    360 gttgttcagc aaaacacgag tagacaagct acacaaggcc gacagaccta tgactggact    420
ttaaatagaa accagcctgc tgcaacagca ttggccaaca caatagaagt gttcagatca    480
aatggcctca cggccaatga gtctggaagg ctcatagact ccttaaggga tgtaatggag    540
tcaatgaaaa aagaagaaat ggggatcaca actcattttc agaaagag acgggtgaga    600 gacaatatga ctaagaaaat gataacacag agaacaatag gtaaaaggaa acagagattg    660
aacaaaagga gttatctaat tagagcattg accctgaaca caatgaccaa agatgctgag    720
agagggaagc taaaacggag agcaattgca accccaggga tgcaaataag ggggtttgta    780
```

-continued

```
tactttgttg agacactggc aaggagtata tgtgagaaac ttgaacaatc agggttgcca      840
gttggaggca atgagaagaa agcaaagttg gcaaatgttg taaggaagat gatgaccaat      900
tctcaggaca ccgaactttc tttgaccatc actggagata caccaaatg gaacgaaaat       960 cagaatcctc ggatgttttt ggccatgatc acatatatga ccagaaatca gcccgaatgg     1020
ttcagaaatg ttctaagtat tgctccaata atgttctcaa acaaaatggc gagactggga     1080
aaagggtata tgtttgagag caagagtatg aaacttagaa ctcaaatacc tgcagaaatg     1140
ctagcaagca ttgatttgaa atatttcaat gattcaacaa gaaagaagat tgaaaaaatc     1200
cgaccgctct aatagaggg gactgcatca ttgagccctg aatgatgat gggcatgttc       1260 aatatgttaa gcactgtatt aggcgtctcc atcctgaatc ttggacaaaa gagatacacc     1320
aagactactt actggtggga tggtcttcaa tcctctgacg attttgctct gattgtgaat     1380
gcacccaatc atgaagggat tcaagccgga gtcgacaggt tttatcgaac ctgtaagcta     1440
catggaatca atatgagcaa gaaaaagtct tacataaaca gaacaggtac atttgaattc     1500
acaagttttt tctatcgtta tgggtttgtt gccaatttca gcatggagct tcccagtttt     1560
ggtgtgtctg ggagcaacga gtcagcggac atgagtattg gagttactgt catcaaaaac     1620
aatatgataa acaatgatct tggtccagca acagctcaaa tggcccttca gttgttcatc     1680
aaagattaca ggtacacgta ccgatgccat agaggtgaca cacaaataca aacccgaaga     1740
tcatttgaaa taaagaaact gtgggagcaa acccgttcca agctggact gctggtctcc      1800 gacggaggcc caaatttata caacattaga aatctccaca ttcctgaagt ctgcctaaaa     1860
tgggaattga tggatgagga ttaccagggg cgtttatgca acccactgaa cccatttgtc     1920
agccataaag aaattgaatc aatgaacaat gcagtgatga tgccagcaca tggtccagcc     1980
aaaaacatgg agtatgatgc tgttgcaaca acacactcct ggatcccca aagaaatcga      2040 tccatcttga atacaagtca agaggagta cttgaagatg aacaaatgta ccaaaggtgc      2100 tgcaattta ttgaaaaatt cttccccagc agttcataca aagaccagt cgggatatcc      2160 agtatggtgg aggctatggt ttccagagcc cgaattgatg cacggattga tttcgaatct     2220
ggaaggataa agaagaaga gttcactgag atcatgaaga tctgttccac cattgaagag     2280
ctcagacggc aaaaatagtg aatttagctt gtccttcatg aaaaaatgcc ttgttcctac     2340
t                                                                    2341
```

<210> SEQ ID NO 6
<211> LENGTH: 2341
<212> TYPE: DNA
<213> ORGANISM: Influenza virus

<400> SEQUENCE: 6

```
agcaaaagca ggcaaaccat ttgaatggat gtcaatccga ctctactgtt cctaaaggtt       60
ccagcgcaaa atgccataag caccacattc ccttatactg gggatcctcc atacagccat      120
ggaacaggaa cagggtacac catggacaca gtcaacagaa cacccaata ttcagagaag       180 gggaagtgga cgacaaatac agaaactggg gcaccccaac tcaacccaat tgatggacca      240
ctacctgagg ataatgagcc aagtggatat gcacaaacag actgtgtcct ggaggctatg      300
gccttccttg aagaatccca cccaggtatc tttgagaact catgccttga acaatggaa       360 gtcgttcaac aaaacagggt ggacaaacta actcaaggtc gccagactta tgattggaca      420
ttaaacagaa tcaaccagc agcaactgca ttagccaaca ccatagaagt ttttagatcg       480
aatggactaa cagctaatga atcaggaagg ctaatagatt tcctcaagga tgtgatggaa      540
```

| | |
|---|---|
| tcaatggata aagaggaaat ggagataaca acacactttc aaagaaaaag gagagtaaga | 600 |
| gacaacatga ccaagaaaat ggtcacacaa agaacaatag gaagaaaaa acaaagagtg | 660 |
| gataagagag gctatctaat aagagctttg acattgaaca cgatgaccaa agatgcagag | 720 |
| agaggtaaat taaaagaag ggctattgca cacccggga tgcaaattag agggttcgtg | 780 |
| tacttcgttg aaactttagc tagaagcatt tgcgaaaagc ttgaacagtc tggactcccg | 840 |
| gttgggggta atgaaaagaa ggccaaactg gcaaatgttg tgagaaaaat gatgactaat | 900 |
| tcacaagaca ctgagctttc tttcacaatc actggggaca cactaagtg aatgaaaat | 960 |
| caaaaccctc gaatgttttt ggcgatgatt acatatatca caaaaatca acctgagtgg | 1020 |
| ttcagaaaca tcctgagcat cgcaccaata atgttctcaa acaaaatggc aagactagga | 1080 |
| aaaggataca tgttcgagag taagaggatg aagctccgaa cacaaatacc cgcagaaatg | 1140 |
| ctagcaagca ttgacctgaa gtatttcaat gaatcaacaa ggaagaaaat tgagaaaata | 1200 |
| aggcctcttc taatagatgg cacagcatca ttgagccctg gatgatgat gggcatgttc | 1260 |
| aacatgctaa gtacggtttt aggagtctcg atactgaatc ttgggcaaaa gaaatacacc | 1320 |
| aagacaacat actggtggga tgggctccaa tcctccgacg attttgccct catagtgaat | 1380 |
| gcaccaaatc atgagggaat acaagcagga gtggatagat tctacaggac ctgcaagtta | 1440 |
| gtgggaatca acatgagcaa aaagaagtcc tatataaata aaacagggac atttgaattc | 1500 |
| acaagctttt tttatcgata tggatttgtg gctaatttta gcatggagct tcccagtttt | 1560 |
| ggagtgtctg gaataaacga gtcagctgat atgagcattg gagtaacagt gataaagaac | 1620 |
| aacatgataa acaatgacct ggaccagca acagcccaga tggctctcca attgttcatc | 1680 |
| aaagactaca gatatacata taggtgccat agaggagaca cacaaattca gacgagaaga | 1740 |
| tcattcgagc taaagaagct gtgggatcaa acccaatcaa gggcaggact attggtatca | 1800 |
| gatgggggac caaacttata caatatccgg aaccttcaca tccctgaagt ctgcttaaag | 1860 |
| tgggagctaa tggatgagaa ttatcaggga agactttgta accccctgaa tcccttttgtc | 1920 |
| agccataaag aaattgagtc tgtaaacaat gctgtagtga tgccagccca tggtccagcc | 1980 |
| aaaagtatgg aatatgatgc cgttgcaact acacactcct ggattcccaa gaggaaccgc | 2040 |
| tctattctca acacaagcca aggggaatt cttgaggatg aacagatgta ccaaaagtgc | 2100 |
| tgcaacttgt ttgagaaatt ttttcctagt agttcatata ggagaccgat ggaatttct | 2160 |
| agcatggtgg aggccatggt gtctagggcc cggattgatg ccagaattga cttcgagtct | 2220 |
| ggacggatta agaaggaaga gttctctgag atcatgaaga tctgttccac cattgaagaa | 2280 |
| ctcagacggc aaaaataatg aatttagctt gtccttcatg aaaaaatgcc ttgtttctac | 2340 |
| t | 2341 |

<210> SEQ ID NO 7
<211> LENGTH: 2341
<212> TYPE: DNA
<213> ORGANISM: Influenza virus

<400> SEQUENCE: 7

| | |
|---|---|
| agcaaaagca ggcaaaccat ttgaatggat gtcaatccga ctctactttt cctaaaggtt | 60 |
| ccagcgcaaa atgccataag caccacattc ccctatactg agatcctcc atacagccat | 120 |
| ggaacaggaa caggatacac catggacaca gtcaacagaa cgcaccaata ttcagaaaaa | 180 |
| gggaagtgga cgacaaacac agaaactggg gcaccccaac tcaacccgat tgatggacca | 240 |

```
ctacctgagg ataatgagcc aagtggatat gcacaaacag actgtgttct ggaggccatg    300
gctttccttg aagaatccca cccagggatc tttgagaact catgccttga acaatggaa    360
gttgttcagc aaacaagggt ggataaacta actcaaggtc gccagactta tgattggaca    420
ttaaacagaa atcaaccggc agcaactgca ttagccaaca ccatagaagt ctttagatcg    480
aatggtctaa cagctaatga gtcaggaagg ctaatagatt tcctaaagga tgtgatggaa    540
tcaatggata agaggaaat agagataaca acacactttc aaagaaaaag agagtaaga     600
gacaacatga ccaagaaaat ggtcacacaa agaacaatag aaagaaaaa acaaagagtg    660
aataagagag gctatttaat aagagcactg acattgaata cgatgaccaa agatgcagag    720
agaggcaaat taaaagaag ggctattgca acacccggga tgcaaatgag agggttcgtg    780
tactttgttg aaactttagc taggagcatt tgcgaaaagc ttgaacagtc tggacttcca    840
gttgggggta atgaaaagaa ggccaaattg gcaaatgttg tgagaaagat gatgactaat    900
tcacaagaca cagagctttc tttcacaatc actggggaca cactaagtg gaatgaaaat    960
caaaatcctc gaatgttcct ggcgatgatt acatatatca caaaaatca acctgagtgg   1020
ttcagaaaca tcctgagcat cgcacccata atgttctcaa acaaaatggc aagactagga   1080
aaagggtaca tgttcgagag taaaagaatg aagctccgaa cacaaatacc agcagaaatg   1140
ctagcaagca ttgacctgaa atatttcaat gaatcaacaa ggaagaaat tgagaaaata   1200
aggcctcttc taatagatgg cacagcatca ttgagccctg aatgatgat gggcatgttc   1260
aacatgctaa gtacggtttt gggagtctcg atactgaatc ttggacaaaa gaaatacacc   1320
aagacaacat actggtggga tgggctccaa tcctccgacg attttgccct catagtgaat   1380
gcaccaaatc atgagggaat acaagcagga gtggatagat tttacaggac ctgcaagtta   1440
gtgggaatca acatgagcaa aaagaagtcc tatataaata agacagggac atttgaattc   1500
acaagctttt tttatcgcta tggatttgtg gctaatttta gcatggagct gcccagtttt   1560
ggagtgtctg gaataaatga atcagctgat atgagcattg gagtaacagt gataagaac   1620
aacatgataa acaatgacct tggaccagca acagcccaga tggccttca attgttcatc   1680
aaagactaca gatatacata tagatgccat agaggagaca cacaaattca gacgagaaga   1740
tcattcgagc taaagaagct gtgggatcaa acccaatcaa aggcaggact attagtgtca   1800
gatggaggac caaacttata caatatccgg aatcttcaca ttcctgaagt ctgcttaaaa   1860
tgggagctaa tggatgagga ttatcgggga agactttgta atcccctgaa tccctttgtc   1920
agccataaag agattgagtc tgtaaacaat gctgtggtga tgccagccca tggtccagcc   1980
aaaagcatgg aatatgatgc cgttgcaact acacactcct ggattcccaa gaggaaccgc   2040
tctattctca acacaagcca agggggaatt cttgaggatg aacagatgta ccagaagtgc   2100
tgcaacctgt tcgagaaatt tttccccagt agttcataca ggagaccggt tggaatttct   2160
agcatggtgg aggccatggt gtctagggcc cggattgatg ccagaattga cttcgagtct   2220
ggaaggatta agaagaaga gttctctgag atcatgaaga tctgttccac cattgaagaa   2280
ctcagacggc aaaaataatg aatttagctt gtccttcatg aaaaaatgcc ttgtttctac   2340
t                                                                 2341
```

<210> SEQ ID NO 8
<211> LENGTH: 2233
<212> TYPE: DNA
<213> ORGANISM: Influenza virus

<400> SEQUENCE: 8

```
agcgaaagca ggtactgatc caaaatggaa gattttgtgc gacaatgctt caatccgatg      60
attgtcgagc ttgcggaaaa acaatgaaag agtatgggg aggacctgaa atcgaaaca      120 aacaaatttg cagcaatatg cactcacttg gaagtatgct tcatgtattc agattttcac    180
ttcatcaatg agcaaggcga gtcaataatc gtagaacttg gtgatccaaa tgcacttttg    240
aagcacagat ttgaaataat cgagggaaga gatcgcacaa tggcctggac agtagtaaac    300
agtatttgca acactacagg ggctgagaaa ccaaagtttc taccagattt gtatgattac    360
aaggagaata gattcatcga aattggagta acaaggagag aagttcacat atactatctg    420
gaaaaggcca ataaaattaa atctgagaaa acacacatcc acattttctc gttcactggg    480
gaagaaatgg ccacaaaggc agactacact ctcgatgaag aaagcagggc taggatcaaa    540
accagactat tcaccataag acaagaaatg gccagcagag gcctctggga ttcctttcgt    600
cagtccgaga gaggagaaga gacaattgaa gaaaggtttg aaatcacagg aacaatgcgc    660
aagcttgccg accaaagtct cccgccgaac ttctccagcc ttgaaaattt tagagcctat    720
gtggatggat tcgaaccgaa cggctacatt gagggcaagc tgtctcaaat gtccaaagaa    780
gtaaatgcta gaattgaacc tttttttgaaa acaacaccac gaccacttag acttccgaat    840
gggcctccct gttctcagcg gtccaaattc ctgctgatgg atgccttaaa attaagcatt    900
gaggacccaa gtcatgaagg agagggaata ccgctatatg atgcaatcaa atgcatgaga    960
acattctttg gatggaagga acccaatgtt gttaaaccac acgaaaaggg aataaatcca  1020
aattatcttc tgtcatggaa gcaagtactg gcagaactgc aggacattga gaatgaggag  1080
aaaattccaa agactaaaaa tatgaagaaa acaagtcagc taaagtgggc acttggtgag  1140
aacatggcac cagaaaaggt agactttgac gactgtaaag atgtaggtga tttgaagcaa  1200
tatgatagtg atgaaccaga attgaggtcg ctagcaagtt ggattcagaa tgagtttaac  1260
aaggcatgcg aactgacaga ttcaagctgg atagagctcg atgagattgg agaagatgtg  1320
gctccaattg aacacattgc aagcatgaga aggaattatt tcacatcaga ggtgtctcac  1380
tgcagagcca cagaatacat aatgaaggg gtgtacatca atactgcctt gcttaatgca  1440
tcttgtgcag caatggatga tttccaatta attccaatga taagcaagtg tagaactaag  1500
gagggaaggc gaaagaccaa cttgtatggt tcatcataaa aaggaagatc ccacttaagg  1560
aatgacaccg acgtggtaaa ctttgtgagc atggagtttt ctctcactga cccaagactt  1620
gaaccacata atgggagaa gtactgtgtt cttgagatag gagatatgct tataagaagt  1680
gccataggcc aggtttcaag gcccatgttc ttgtatgtga gaacaaatgg aacctcaaaa  1740
attaaaatga atgggggaat ggagatgagg cgttgcctcc tccagtcact tcaacaaatt  1800
gagagtatga ttgaagctga gtcctctgtc aaagagaaag acatgaccaa agagttcttt  1860
gagaacaaat cagaaacatg gcccattgga gagtccccca aggagtggga ggaaagttcc  1920
attgggaagg tctgcaggac tttattagca agtcggtat tcaacagctt gtatgcatct  1980
ccacaactag aaggattttc agctgaatca agaaaactgc ttcttatcgt tcaggctctt  2040
agggacaacc ttgaacctgg gacctttgat cttgggggc tatatgaagc aattgaggag  2100
tgcctgatta atgatccctg ggttttgctt aatgcttctt ggttcaactc cttccttaca  2160
catgcattga gttagttgtg gcagtgctac tatttgctat ccatactgtc caaaaaagta  2220 ccttgttct act                                                      2233
```

<210> SEQ ID NO 9

<211> LENGTH: 2233
<212> TYPE: DNA
<213> ORGANISM: Influenza virus

<400> SEQUENCE: 9
agcaaaagca ggtactgatt cgaaatggaa gattttgtgc gacaatgctt caacccgatg 60
attgtcgaac ttgcagaaaa aacaatgaaa gagtatggag aggatctgaa aattgaaaca 120
aacaaatttg cagcaatatg cacccacttg gaggtatgtt tcatgtattc agattttcat 180
ttcatcaatg aacaaggcga atcaataatg gtagaacttg atgatccaaa tgcactgtta 240
aagcacagat tcgaaataat cgaggggaga gacagaacaa tggcctggac agtagtaaac 300
agtatctgca acactactgg agctgaaaaa ccgaagtttc taccagattt gtatgattac 360
aaggagaaca gattcatcga aattggagtg acaagaagag aagtccacat atattacctt 420
gaaaaggcca ctaaaattaa atctgagaac acacacattc acattttctc attcactggg 480
gaggaaatgg ccacaaaggc agactacact ctcgacgagg aaagcagggc taggattaaa 540
accaggctat ttaccataag acaagaaatg gccaacagag gcctctggga ttcctttcgt 600
cagtccgaaa gaggcgaaga aacaattgaa gaaaaatttg aaatctcagg aactatgcgt 660
aggcttgccg accaaagtct cccaccgaac ttctcctgcc ttgagaattt tagagcctat 720
gtggatggat tcgaaccgaa cggctgcatt gagggcaagc tttctcaaat gtccaaagaa 780
gtgaatgcca aaattgaacc ttttctgaag acaacaccaa gaccaatcaa acttcctaat 840
ggacctcctt gttatcagcg gtccaaattc ctcctgatgg atgctttgaa attgagcatt 900
gaagacccaa gtcacgaagg agaagggatt ccattatatg atgcgatcaa gtgcataaaa 960
acattctttg gatggaaaga accttatata gtcaaaccac acgaaaaggg aataaattca 1020
aattacctgc tgtcatggaa gcaagtattg tcagaattgc aggacattga aaatgaggag 1080
aagatcccaa ggactaaaaa catgaagaaa acgagtcaac taaagtgggc tcttggtgaa 1140
aacatggcac cagagaaagt agactttgac aactgcagag acataagcga tttgaagcaa 1200
tatgatagtg acgaacctga attaaggtca ctttcaagct ggatacagaa tgagttcaac 1260
aaggcctgcg agctaactga ttcaatctgg atagagctcg atgaaattgg agaggacgta 1320
gccccaattg agtacattgc aagcatgagg aggaattatt tcacagcaga ggtgtcccat 1380
tgtagagcca ctgagtacat aatgaagggg gtatacatta atactgccct gctcaatgca 1440
tcctgtgcag caatggacga ttttcaatta atccccatga taagcaagtg cagaactaaa 1500
gagggaaggc gaaaaaccaa tttatatgga ttcatcataa agggaagatc tcatttaagg 1560
aatgacacag atgtggtaaa ctttgtgagc atggaatttt ctctcactga cccgagacta 1620
gagccacata aatgggagaa atactgtgtc cttgagatag gagatatgtt actaagaagt 1680
gccataggcc aaatttcaag gcctatgttc ttgtatgtta ggacaaacgg aacatcaaag 1740
gtcaaaatga aatggggaat ggagatgaga cgttgcctcc ttcagtcact ccagcagatc 1800
gagagcatga ttgaagccga gtcctcgatt aaagagaaag acatgaccaa agagtttttt 1860
gagaataaat cagaagcgtg gcccattggg gagtccccca agggagtgga agaaggttcc 1920
attgggaaag tctgtaggac tctattggct aagtcagtgt tcaatagcct gtatgcatca 1980
ccacaattgg aaggattttc agcggagtca agaaaactgc ttcttgttgt tcaggctctt 2040
agggacaacc tcgaacctgg gacctttgat ctcggggggc tatatgaagc aattgaggag 2100
tgcctgatta atgatccctg ggttttgctc aatgcatctt ggttcaactc cttcctgaca 2160
catgcattaa aatagttatg gcagtgctac tatttgttat ccgtactgtc caaaaaagta 2220

```
ccttgtttct act                                                          2233

<210> SEQ ID NO 10
<211> LENGTH: 2233
<212> TYPE: DNA
<213> ORGANISM: Influenza virus

<400> SEQUENCE: 10
agcaaaagca ggtactgatt cgaaatggaa gattttgtgc gacaatgctt caacccgatg         60
attgtcgaac ttgcagaaaa ggcaatgaaa gagtatggag aggatctgaa aattgaaaca        120
aacaaatttg cagcaatatg cactcacttg gaggtatgtt tcatgtattc agattttcat        180
ttcatcaatg aacaaggtga atcaatagtg gtagaacttg acgatccaaa tgcactgtta        240
aagcacagat ttgaaataat agaggggaga gacagaacga tggcctggac agtagtaaac        300
agtatctgca cactactggg agctgagaaa ccgaagtttc tgccagattt gtatgattac        360
aaggagaaca gattcatcga aattggagta caaggagaa aagtccacat atattacctt        420
gaaaaggcca ataaaattaa atctgagaat acacacatcc acattttctc attcactggg        480
gaggaaatgg ccacaaaggc agactacact ctcgacgagg aaagcagggc taggattaag        540
accaggctat ttaccataag acaagaaatg ccaacagag gcctctggga ttcctttcgt        600
cagtccgaaa gaggcgaaga gacaattgaa gaaaatttg aaatctcagg aactatgcgc        660
aggcttgccg accaaagcct cccgccgaac ttctcctgcc ttgagaattt tagagcctat        720
gtagatggat tcgaaccgaa cggctgcatt gagggcaagc tttctcaaat gtccaaagaa        780
gtgaatgcca aaattgaacc ttttctgaag acaacaccaa gaccaatcaa acttccgaat        840
ggacctcctt gttatcagcg gtccaaattc cttctgatgg atgctttaaa attaagcatt        900
gaagacccaa gtcatgaagg agaagggata ccactatatg atgcgatcaa gtgcataaga        960
acattctttg gatggaaaga accctatata gtcaaaccac acgaaaaggg aataaattca       1020
aattacctgc tgtcatggaa gcaagtactg gcagaattgc aggacattga aactgaggag       1080
aagattccaa gaactaaaaa catgaagaaa acgagtcaac taagtgggc tcttggtgaa       1140 aacatggcac cagagaaagt agactttgac aactgcagac ataagcga tttgaagcaa       1200 tatgatagtg acgaacctga attgaggtca ctttcaagct ggatacagaa tgagttcaac       1260
aaggcatgcg agctgactga ttcaatctgg ataagagctcg atgaaattgg agaagacata       1320
gccccaattg agtacattgc aagcatgagg aggaattatt tcacagcaga ggtgtcccac       1380
tgcagagcca ctgagtacat aatgaagggg gtatacatta atactgcctt gctcaatgca       1440
tcctgtgcag caatggacga ttttcaacta attcccatga taagcaagtg cagaacaaaa       1500
gagggaaggc gaaaaccaa tttatatgga ttcatcataa aagggagatc tcacttaagg       1560
aatgacacag atgtggtaaa ctttgtgagc atggagttt ctctcactga cccgaggctt       1620
gagccacata atgggagaa atactgtgtc cttgagatag gagatatgtt actaagaagt       1680
gccataggcc aaatgtcaag gcctatgttc ttgtatgtga ggacaaatgg aacatcaaag       1740
atcaaaatga aatggggaat ggagatgaga cgttgcctcc ttcagtcact ccagcagatc       1800
gagagcatga ttgaagccga gtcctcggtt aaagagaaag acatgaccaa agagtttttt       1860
gagaataaat cagaagcatg gcccattggg agtccccca agggagtgga agaaggttcc       1920
attgggaaag tttgtaggac tttgttggct aagtcggtgt caatagcct gtatgcatct       1980 ccacaattag aaggattttc agcggagtca agaaaactgc tccttgttgt tcaggctctt       2040
```

```
agggacaacc ttgaacctgg gacctttgat cttgggggc tatatgaagc aattgaggag    2100
tgcctgatta atgatccctg ggttttgctc aatgcgtctt ggttcaactc cttcctgaaa    2160
catgcattaa aatagttatg gcagtgctac tatttgttat ccatactgtc caaaaagta    2220 ccttgtttct act                                                       2233
```

```
<210> SEQ ID NO 11
<211> LENGTH: 31
<212> TYPE: DNA
<213> ORGANISM: Artificial Sequence
<220> FEATURE:
<223> OTHER INFORMATION: Primer

<400> SEQUENCE: 11
atggtctcta ctgatggtga gcaagggcga g                                   31

<210> SEQ ID NO 12
<211> LENGTH: 34
<212> TYPE: DNA
<213> ORGANISM: Artificial Sequence
<220> FEATURE:
<223> OTHER INFORMATION: Primer

<400> SEQUENCE: 12
atgaagacaa tctcttactt gtacagctcg tcca                                34

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
ggacacgctg aacttgtgg                                                 19

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
agataagagg ataatggaaa tg                                             22

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
atatggtcca ckgtggtttt tg                                             22

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
ggagaagact gagggattc                                                 20
```

```
<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
tccatggtgt atcctgttcc                                              20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tgatttcgaa tctggaagga                                              20

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
tgagtgcata ttgctgcaaa t                                            21

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
ttcttatcgt tcaggctctt                                              20

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
tccagtatgg ttttgayttc cr                                           22

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
tggactagtg sgagcatsat                                              20

<210> SEQ ID NO 23
<211> LENGTH: 20
<212> TYPE: DNA
<213> ORGANISM: Artificial Sequence
<220> FEATURE:
```

```
<223> OTHER INFORMATION: Primer

<400> SEQUENCE: 23
tcccaggcgg tctcccatcc                                                   20

<210> SEQ ID NO 24
<211> LENGTH: 395
<212> TYPE: RNA
<213> ORGANISM: Influenza virus

<400> SEQUENCE: 24
agcgaaagca ggucaaauau auucaauaug gaaagaauaa aagaacuaag aaaucuaaug        60
ucgcagucuc gcacccgcga gauacucaca aaaaccaccg uggaccauau ggccauaauc       120
aagaaguaca caucaggaag acaggagaag acugagggga uuccucauuc ugggcaaaga       180
ggacaagaga uaugggccag cacuaagcau caaugaacug agcaaccuug cgaaaggaga       240
gaaggcuaau gugcuaauug ggcaagggga uguggguug guaaugaaac ggaaacggga       300
cucuagcaua cuuacugaca gccagacagc gaccaaaaga auucggaugg ccaucaauua       360
gugucgaaua guuuaaaaac gaccuuguuu cuacu                                 395

<210> SEQ ID NO 25
<211> LENGTH: 62
<212> TYPE: PRT
<213> ORGANISM: Influenza virus

<400> SEQUENCE: 25

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
                20                  25                  30

Lys Tyr Thr Ser Gly Arg Gln Glu Lys Thr Glu Gly Ile Pro His Ser
            35                  40                  45

Gly Gln Arg Gly Gln Glu Ile Trp Ala Ser Thr Lys His Gln
        50                  55                  60
```